United States Patent [19]
Maas

[11] Patent Number: 5,857,990
[45] Date of Patent: Jan. 12, 1999

[54] ORTHOPEDIC GARMENT FOR DYNAMIC SCAPULAR AND ACROMIO-CLAVICULAR STABILIZATION, INCLUDING DYNAMICALLY ENHANCING PROPER POSTURE

[76] Inventor: Richard D. Maas, 2525 Chapel Ave., Springfield, Mo. 65809

[21] Appl. No.: 879,102

[22] Filed: Jun. 19, 1997

Related U.S. Application Data

[60] Provisional application No. 60/020,160 Jun. 20, 1996 and provisional application No. 60/025,385 Sep. 4, 1996.

[51] Int. Cl.$^6$ .............................. A01F 13/60; A01F 5/00
[52] U.S. Cl. .................................. 602/62; 602/61; 602/4; 602/20
[58] Field of Search ................................. 602/2, 4, 5, 20, 602/61, 62; 128/869, 874, 877, DIG. 19; 2/44, 45

[56] References Cited

U.S. PATENT DOCUMENTS

| | | | |
|---|---|---|---|
| 50,128 | 9/1865 | Hudson | 602/4 |
| 2,980,426 | 4/1961 | Johnson | 602/4 |
| 4,198,964 | 4/1980 | Honneffer | 128/DIG. 19 X |
| 4,446,858 | 5/1984 | Verter | 602/4 |
| 4,735,198 | 4/1988 | Sawa . | |
| 4,947,870 | 8/1990 | Larcher | 128/DIG. 19 X |
| 5,018,513 | 5/1991 | Charles | 2/45 X |
| 5,095,894 | 3/1992 | Marble | 602/20 |
| 5,188,587 | 2/1993 | McGuire et al. | 602/4 X |
| 5,403,268 | 4/1995 | Clement | 602/20 |
| 5,407,420 | 4/1995 | Bastyr et al. | 602/5 |
| 5,599,286 | 2/1997 | Labelle et al. | 602/5 X |
| 5,628,725 | 5/1997 | Ostergard | 602/26 |

*Primary Examiner*—Richard J. Apley
*Assistant Examiner*—Denise Pothier
*Attorney, Agent, or Firm*—Jonathan A. Bay

[57] ABSTRACT

An orthopedic base garment and strap system is provided for treating pathologies of the scapula, shoulder girdle, or upper trunk or quadrant or else which affects posture. The system includes an elastic base garment that has at least one upper arm encircling portion, a torso encircling portion, and an arm-and-shoulder portion spanning between and interconnecting the upper arm encircling and torso encircling portions. The base garment has diverse inner and outer surfaces such that the inner surface is adapted for high friction contact with the patient's skin or else with a thin undergarment worn by the patient, whereas the outer surface is provided with hook-fastener securing areas. The torso encircling portion is configured as opposite belt straps, one of which belt straps has hook fasteners. That way, the belt straps allow releasable formation of a belt around the patient's torso underneath and clear of the breasts. The system includes not only the elastic base garment but also one or more auxiliary straps of assorted lengths and which have hook-fastener compatible ends for securing to the base garment in diverse arrangements. These straps are elastic in order to allow adjusting the compression against the patient in order to sufficiently enhance dynamical positioning of the posture and/or dynamical stabilization of the scapula.

17 Claims, 20 Drawing Sheets

(Front)

(Rear)

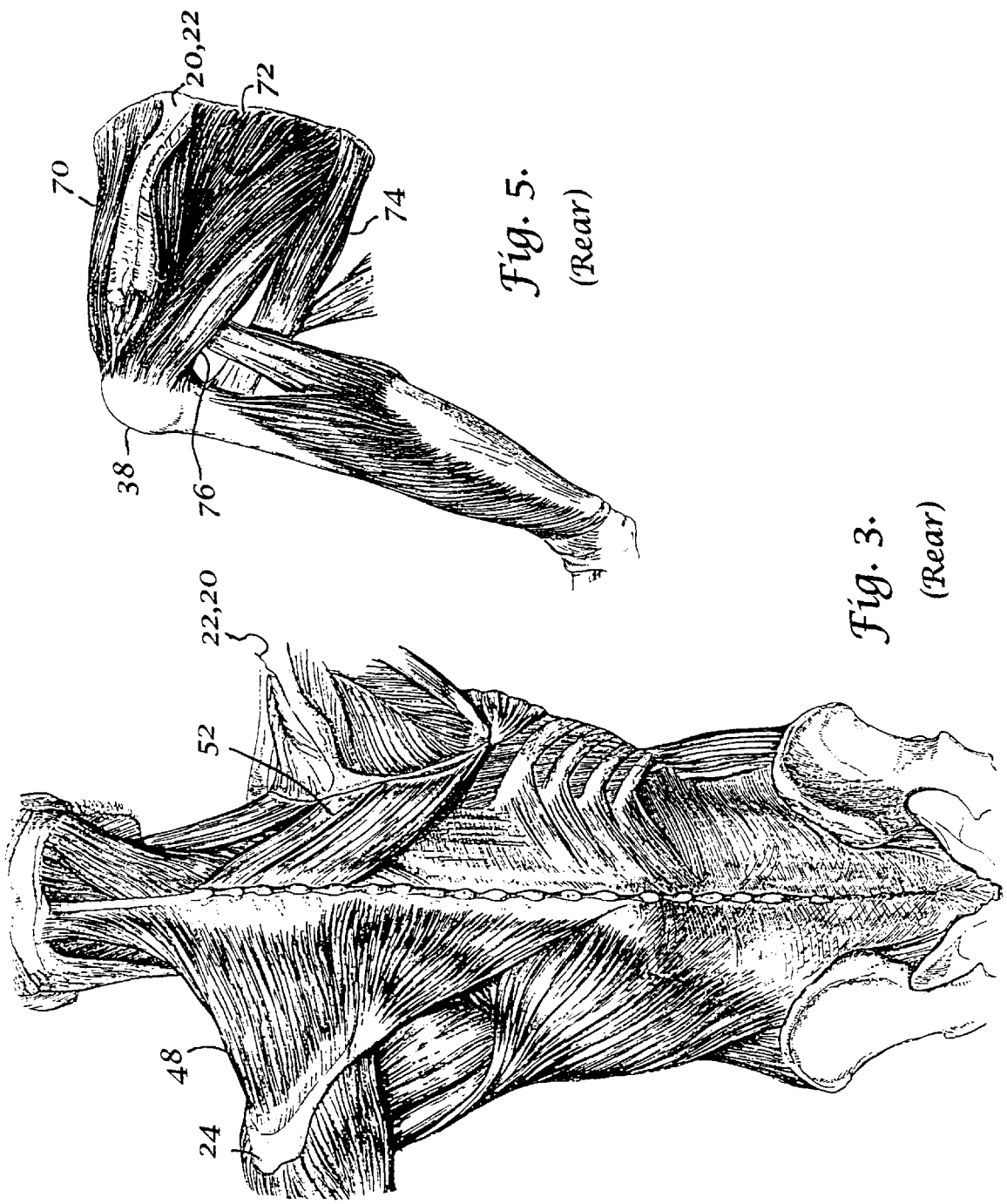

(Front)

(Front)

(Front)

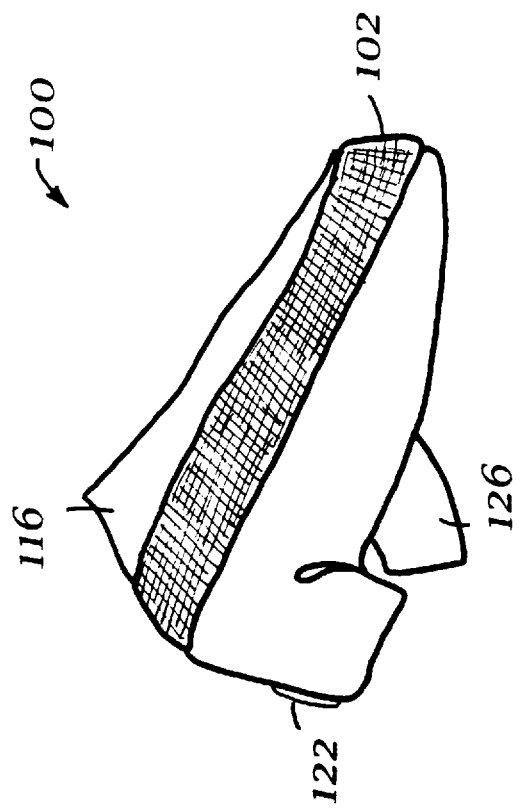
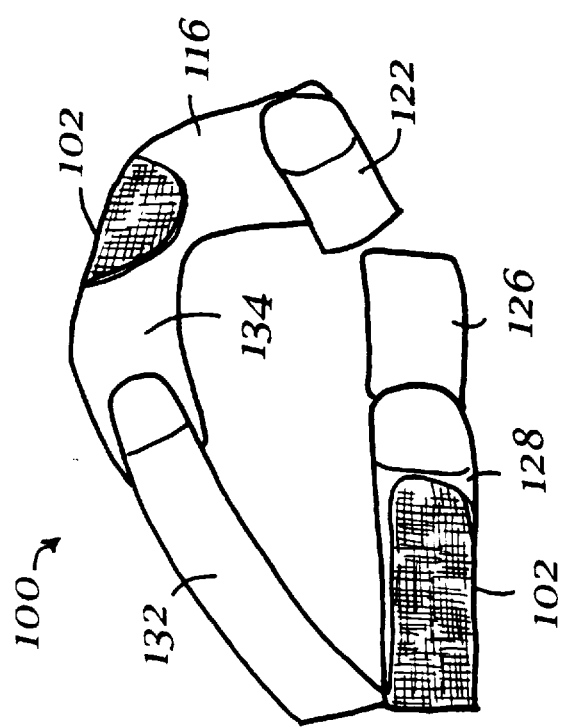

(Front)

(Rear)

(Front)

(Rear)

(Front)

(Rear)

(Front)
normal (Front)
type I (Front)
type II (Front)
type III

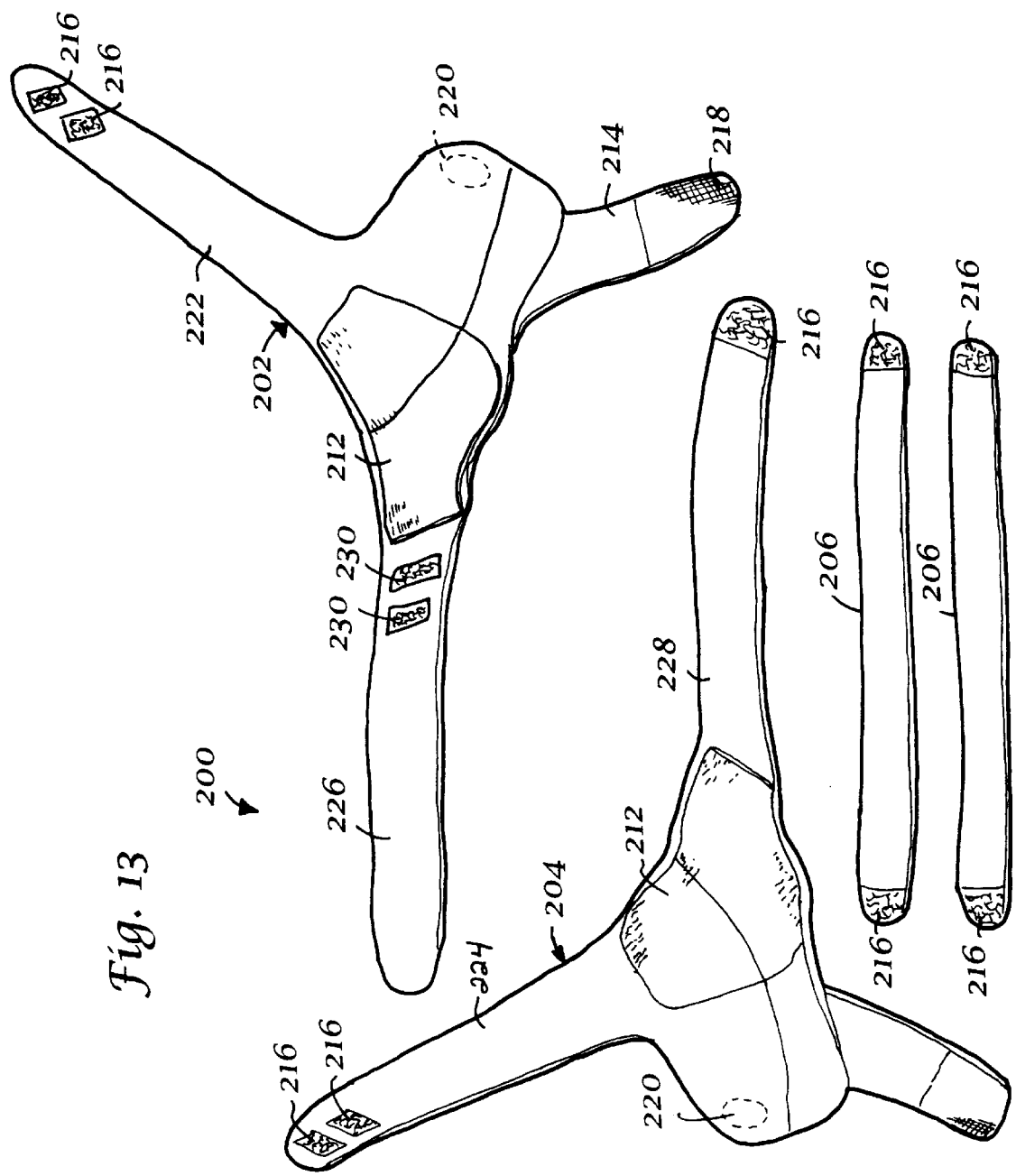

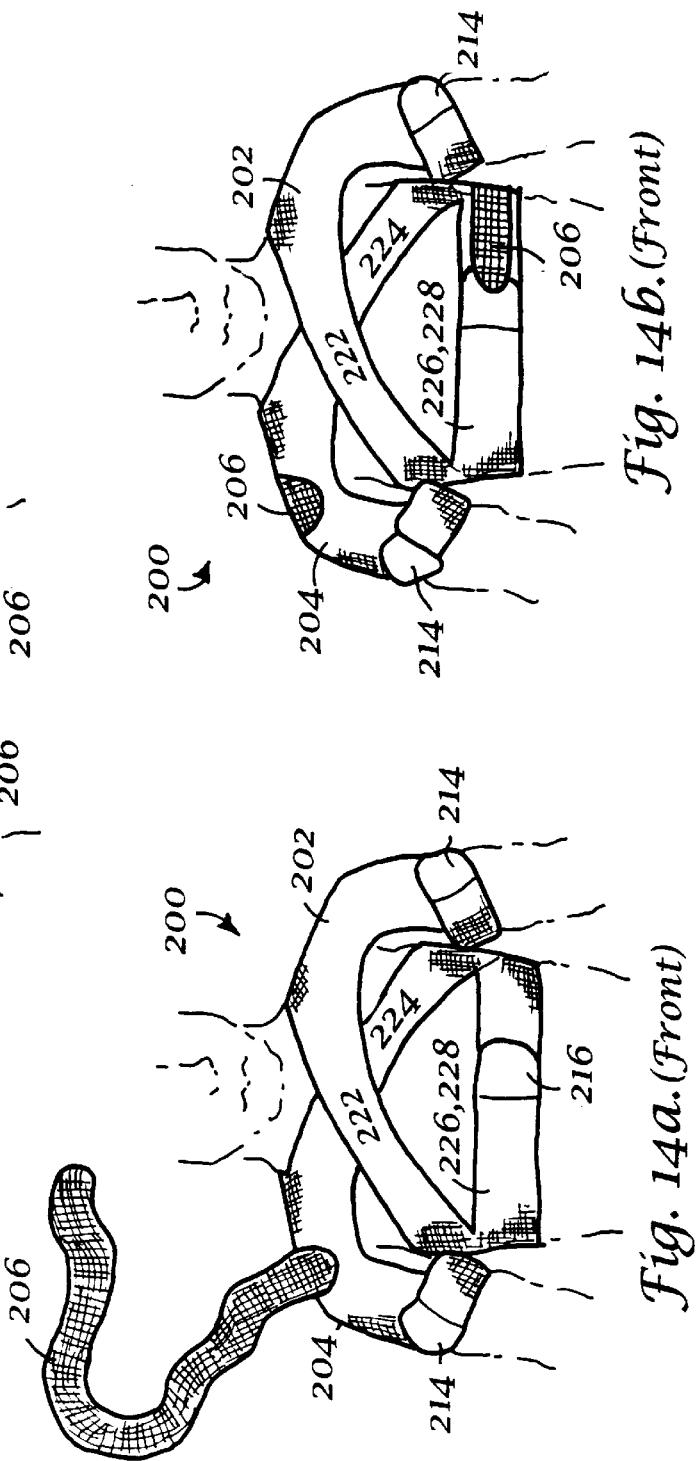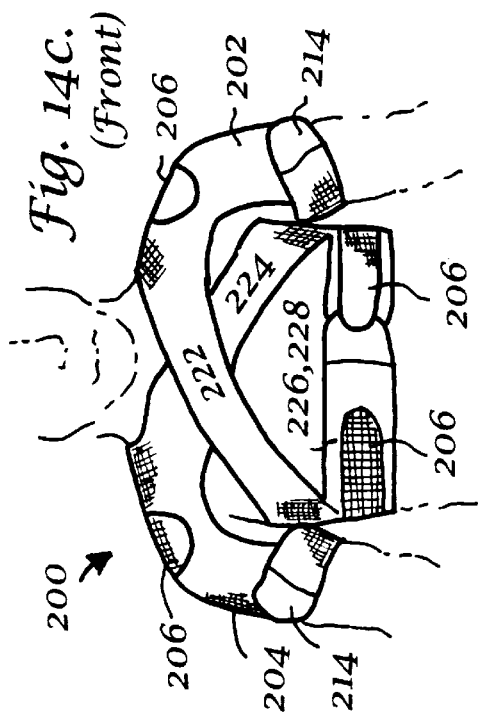

(Rear)

(Rear)

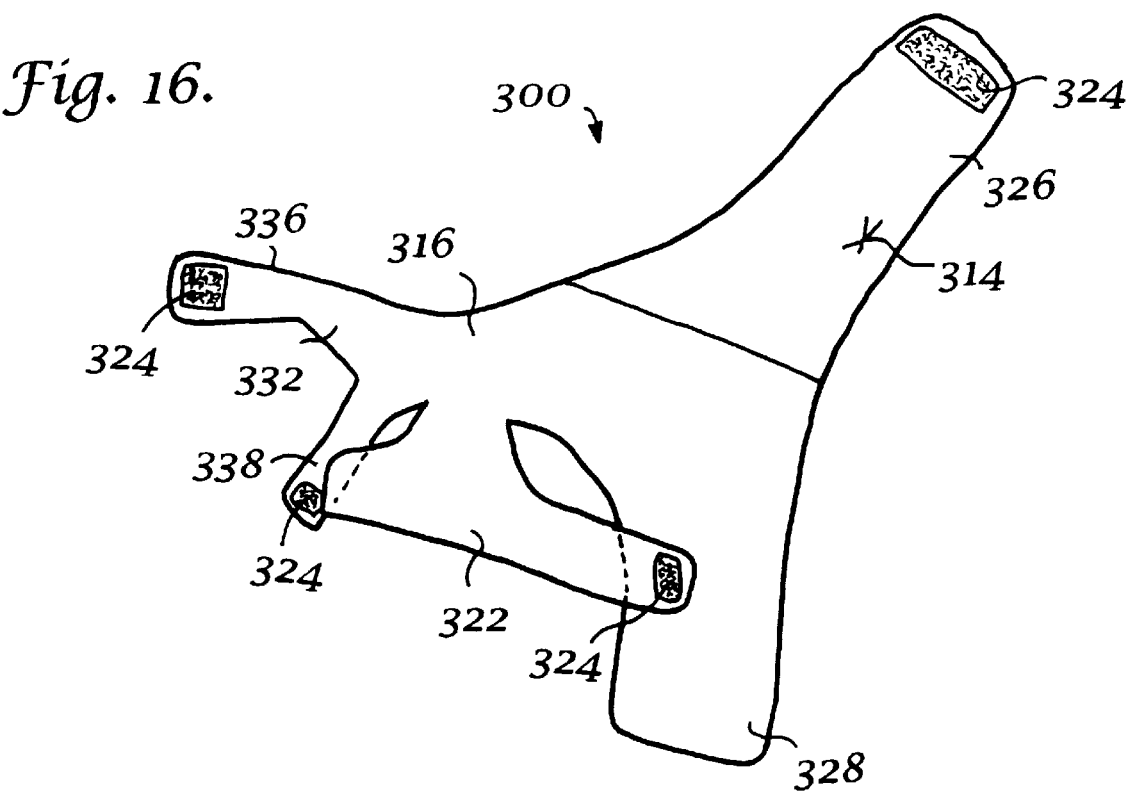
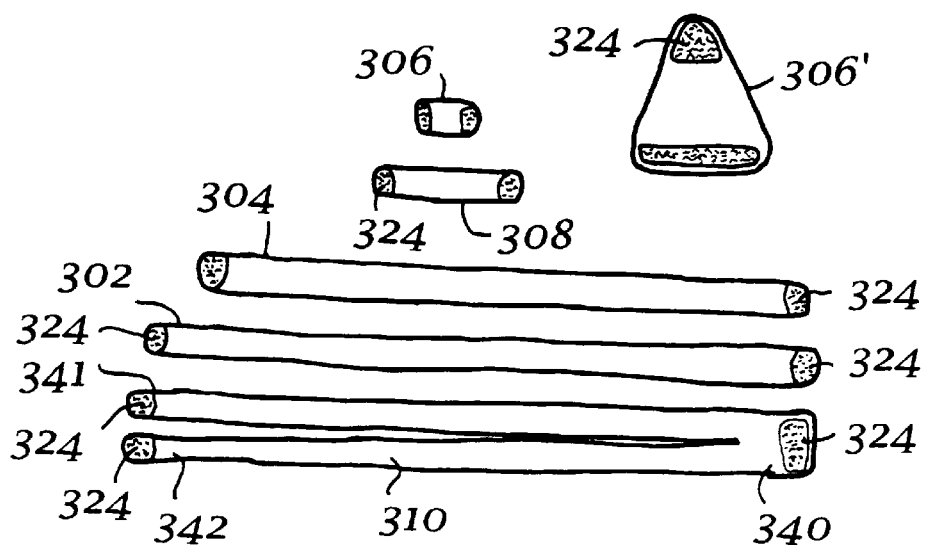
Fig. 16.

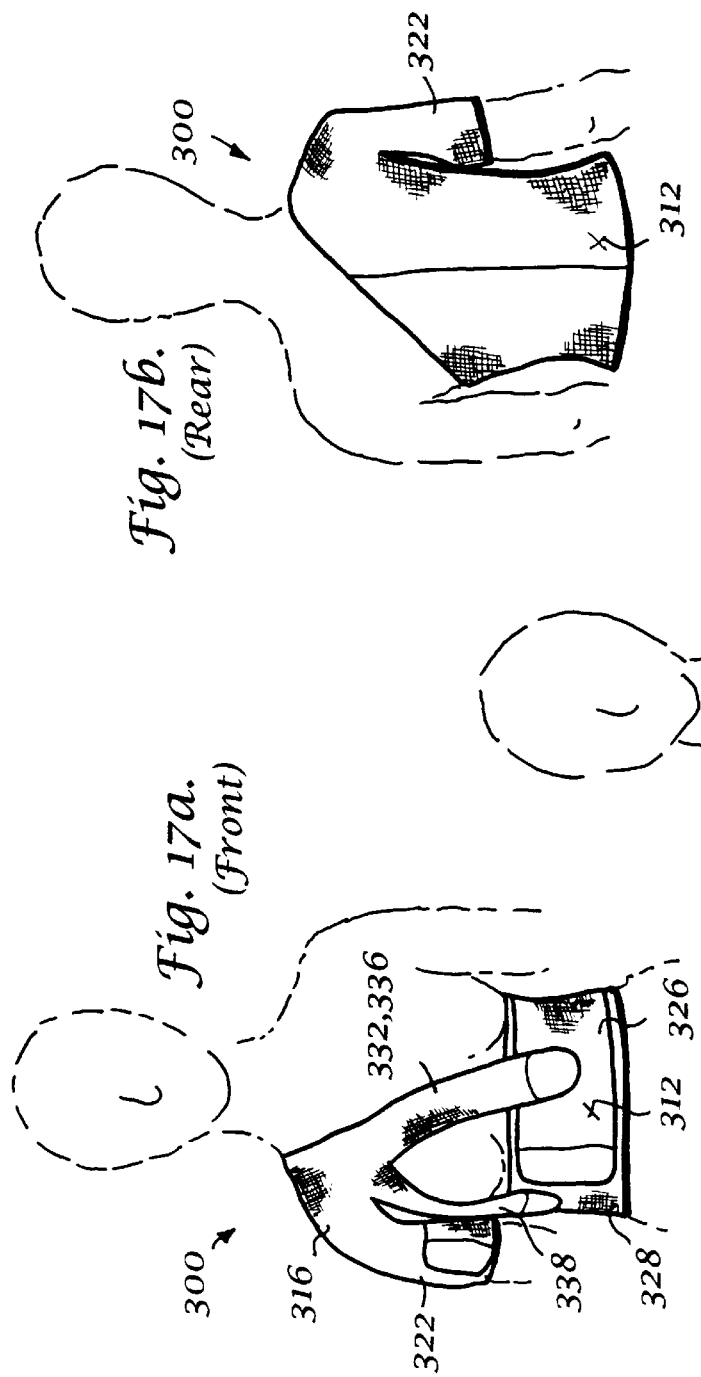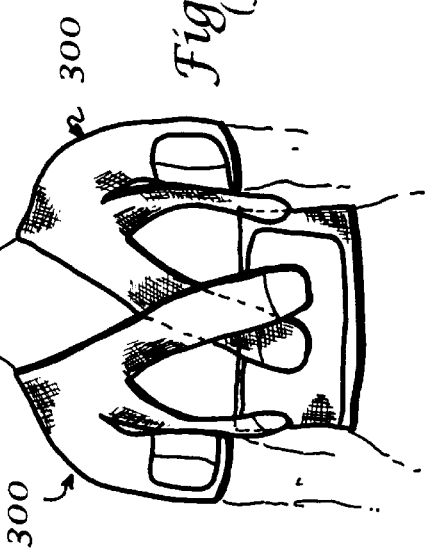

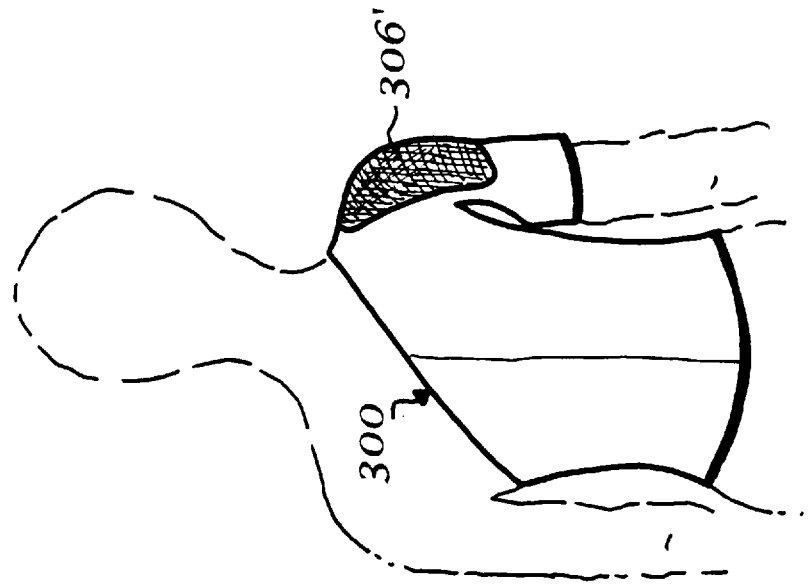
Fig. 19b. (Rear)
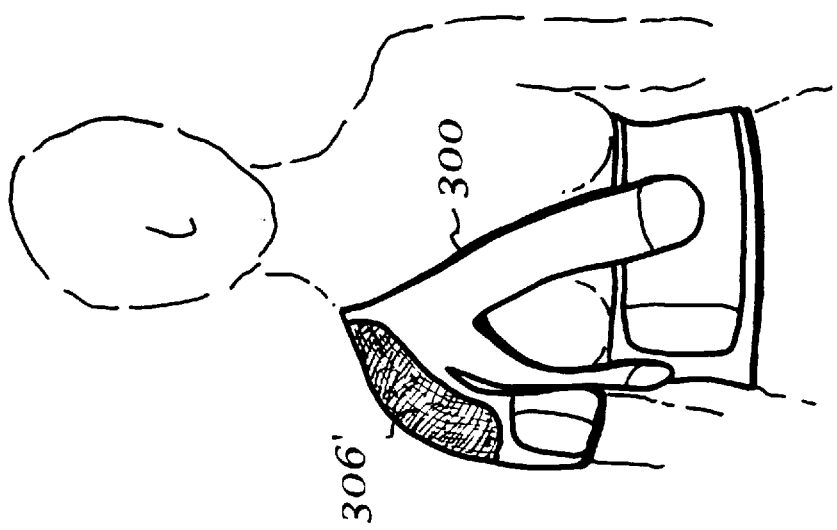
Fig. 19a. (Front)

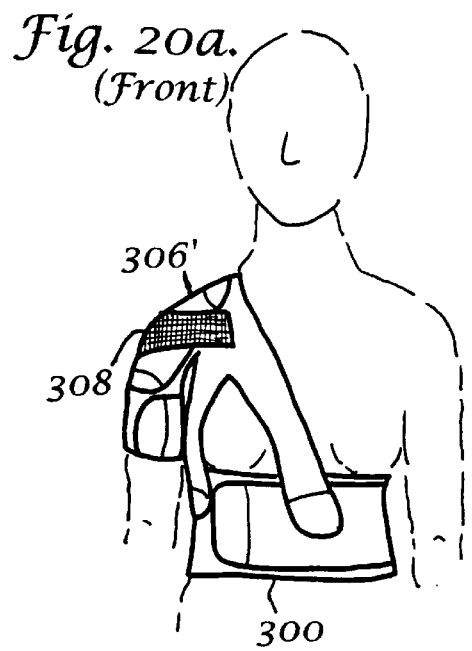
Fig. 20a. (Front)
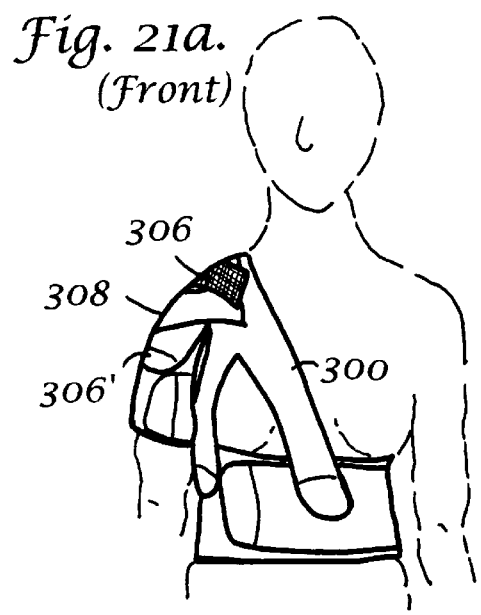
Fig. 21a. (Front)
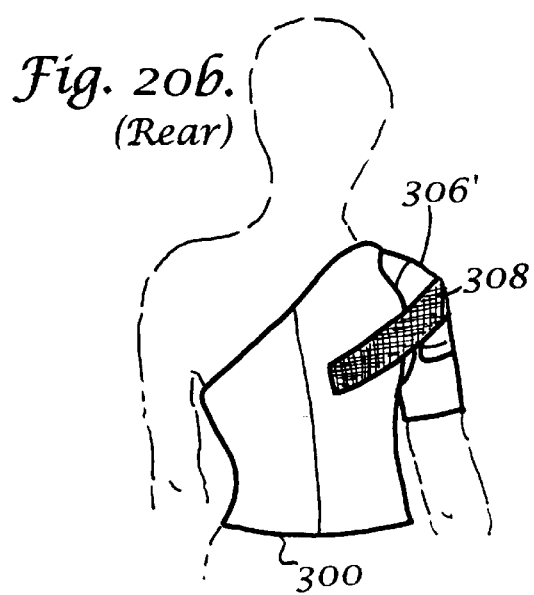
Fig. 20b. (Rear)
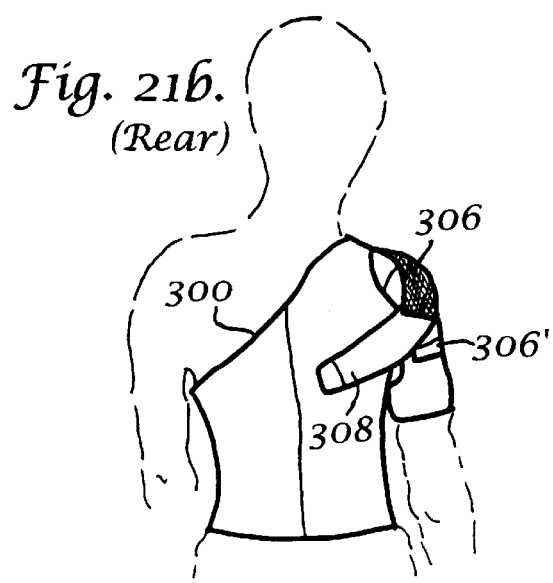
Fig. 21b. (Rear)

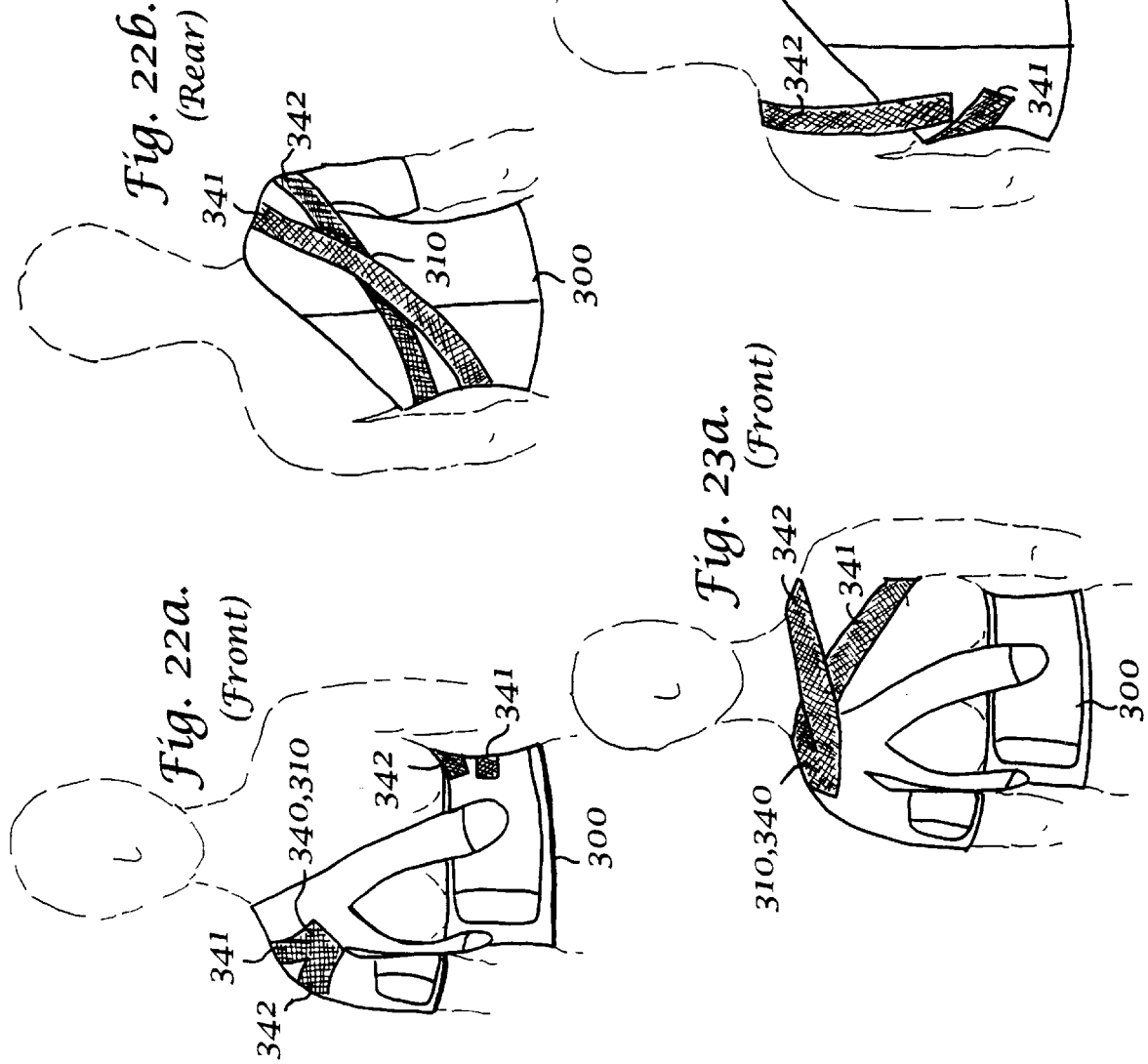

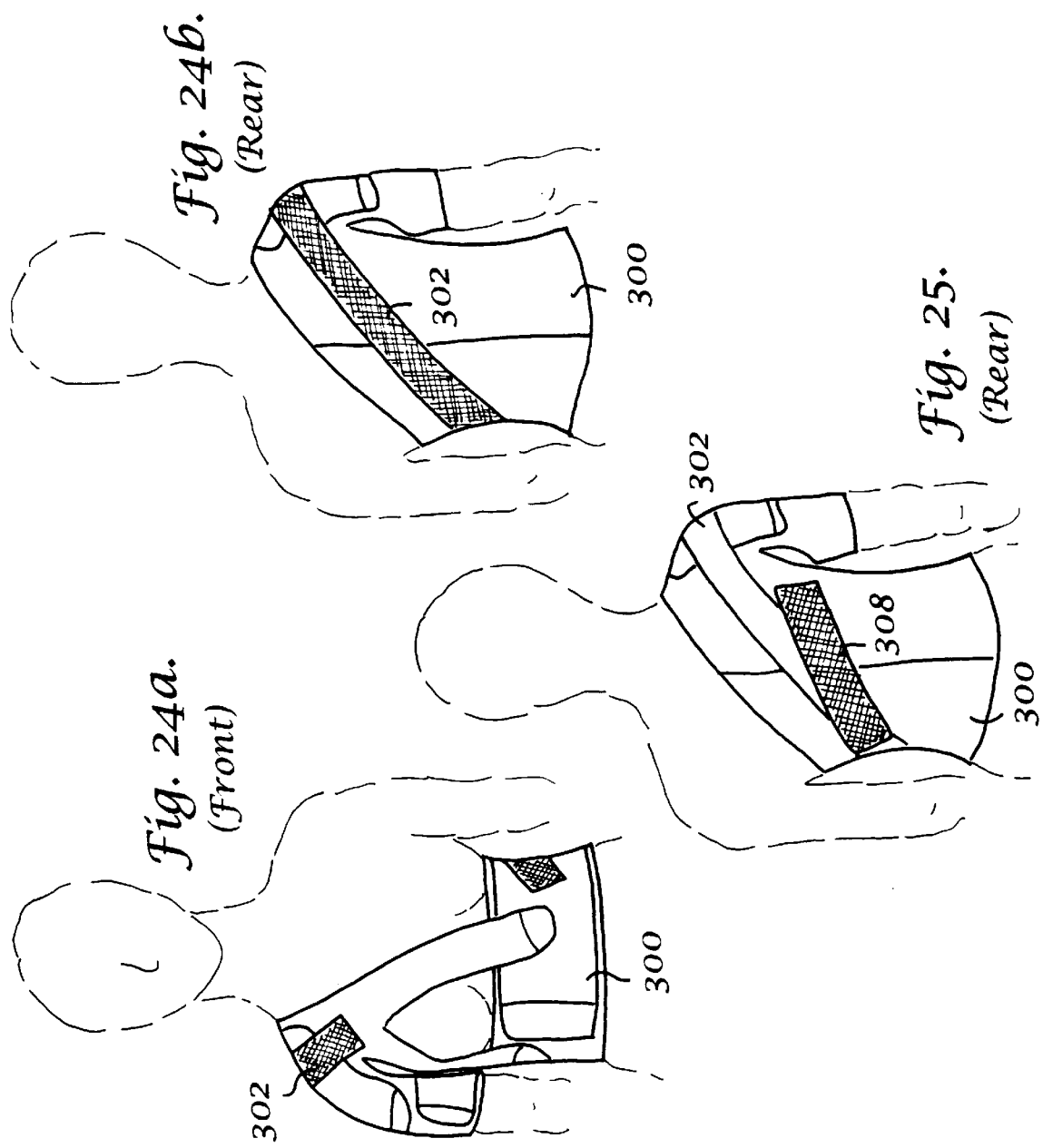

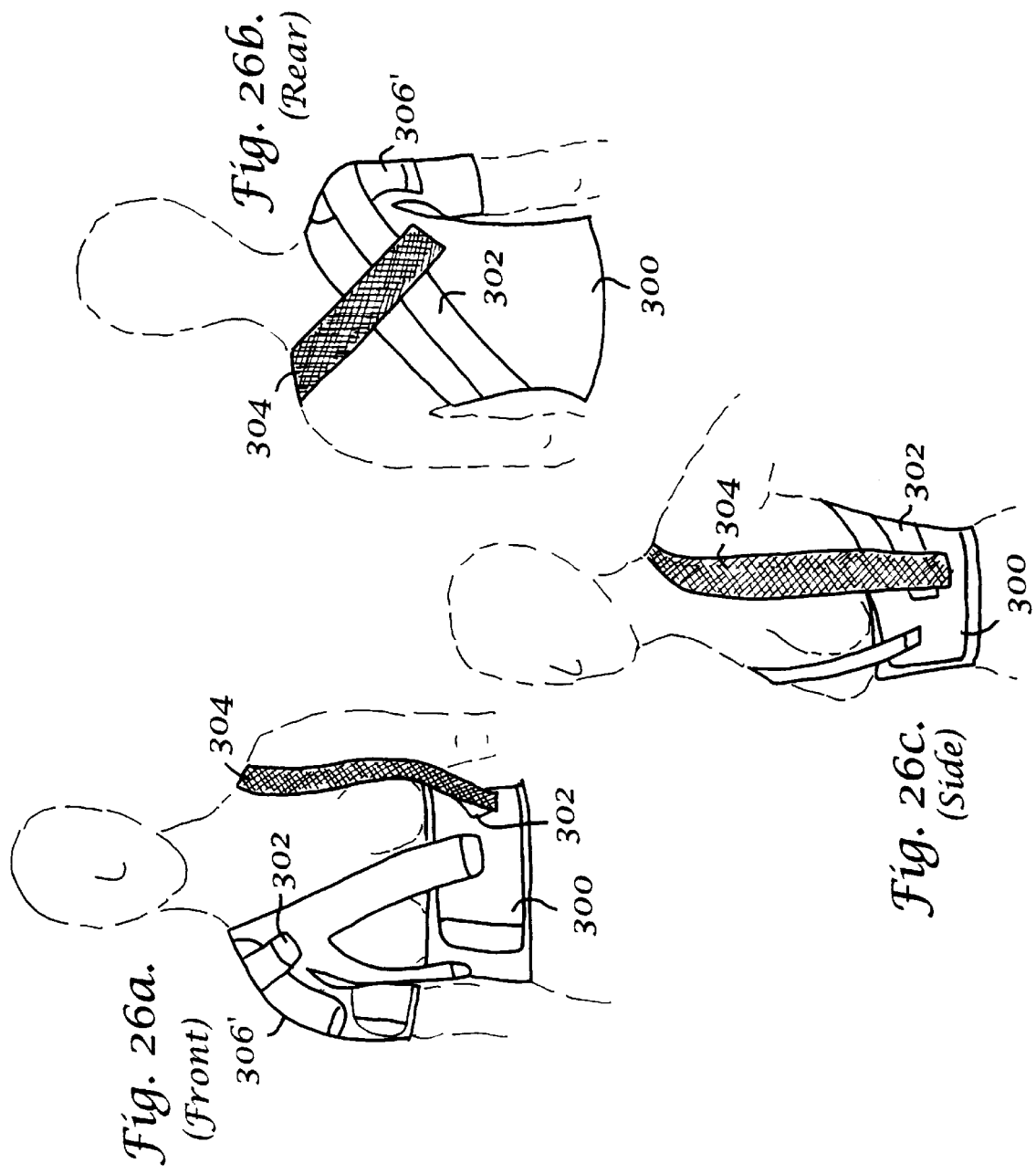

ORTHOPEDIC GARMENT FOR DYNAMIC SCAPULAR AND ACROMIO-CLAVICULAR STABILIZATION, INCLUDING DYNAMICALLY ENHANCING PROPER POSTURE

CROSS-REFERENCE TO PROVISIONAL APPLICATION(S)

This application claims the benefit of U.S. Provisional application Ser. No. 60/020,160, filed Jun. 20, 1996, and U.S. Provisional application Ser. No. 60/025,385, filed Sep. 4, 1996.

BACKGROUND OF THE INVENTION

1. Field of the Invention

The invention relates to orthopedic braces, splints and bandages or the like, and, more particularly, to an elastomeric, orthopedic garment for disorders associated with the upper extremity, including the shoulder girdle. An orthopedic garment in accordance with the invention is provided for supporting and stabilizing the spine and/or one or more given articulations of the upper extremity that have a given disorder, malalignment and/or dysfunction, including without limitation dynamic scapular and acromio-clavicular stabilization, as well as dynamically enhancing proper posture. In other words, the given articulations include but are not limited to a group of joints or ligaments comprising the acromio-clavicular articulation, the coraco-clavicular ligaments, the shoulder joint, and the sterno-clavicular articulation. A central bone among this group of joints and ligaments is the shoulder blade bone, more properly called the "scapula."

2. Prior Art

As various terms of art are used in this written description, some more difficult than others, what follows is a brief overview of the pertinent anatomy, as presented and explained with general reference to FIGS. 1 through 5.

The bones that constitute the "upper extremity" of the human body consist of those of the shoulder girdle, the arm, the forearm and the hand. The shoulder girdle itself consists of two bones, the clavicle and scapula. FIG. 1 shows a rear view of a left scapula 20. The left scapula 20, as representative of a right scapula, is a large, generally flat or planar bone, triangular in shape, situated on the back of the rib cage (not shown) at an upper left border. The scapula 20 generally defines a plane; however, close examination reveals that the scapula 20 is slightly convex (from the rear view vantage point of FIG. 1). The scapula 20's rear surface is subdivided unequally by a spine 22 into two parts. The scapula 20 extends left to right in FIG. 1 between an internal or vertebral border and an external or axillary (i.e., arm pit) border. The spine 22 originates near the internal or vertebral border, and increases in mass as it extends to the external or axillary border, to where, at the margin of the external border, the spine 22 diverges from the plane of the scapula 20 and projects outward or beyond the external border to terminate in a prominence of bone mass, or a bone process formally called the acromion process 24.

The acromion process 24 is formed on its front surface with a concavity (not in view, but occurring at the position indicated by arrow 26) that forms an articulation with the outer extremity of the left clavicle 34 (not shown in FIG. 1, but see FIG. 2). The external or axillary border of the scapula 20 is formed with a cavity 36 called the glenoid cavity. The glenoid cavity 36 is spaced downwardly and slightly forwardly from the acromion process 24 and is the socket which forms the articulation with the humeral head 38 or "ball" (see FIG. 2) in the ball-and-socket joint of the shoulder. Above and in front of the glenoid cavity there is another prominence of bone mass or bone process, called the coracoid process 42.

FIG. 2 shows various articulations of the upper extremity, including the acromio-clavicular articulation 44, the coraco-clavicular ligaments 46, and the shoulder joint. The acromio-clavicular articulation 44 is formed between the outer extremity of the clavicle 34 and the front surface of the acromion process 24, and the ligaments of this articulation are collectively called the acromio-clavicular ligaments. The coraco-clavicular ligaments 46 serve to connect the clavicle 34 with the coracoid process 42 of the scapula 20.

The shoulder joint, as previously mentioned, is a ball-and-socket joint formed by the large globular head of the humerus 38, and the glenoid cavity 36 in the scapula 20, which receives the humeral head 38. The ligaments of the shoulder include a capsular ligament, a coraco-humeral ligament, a glenoid labrum (not shown), as well as the long tendon from the biceps. The capsular ligament generally encircles the ball-and-socket structure, and extends between the circumference of the glenoid cavity 36 in the scapula 20 and the anatomical neck of the humerus. The coraco-humeral ligament is a broad band which reinforces the upper part of the capsular ligament. The glenoid labrum (not shown) is a rim attached round the margin of the glenoid cavity. The long tendon of the biceps inserts as shown and becomes continuous with the glenoid labrum.

FIGS. 3, 4a and 4b show the muscles of the upper trunk, in which FIG. 3 shows the muscles of the upper back and FIGS. 4a and 4b the front of the chest.

With reference to FIG. 3, the muscles of the back are numerous and are for classification purposes subdivided in five layers, only the outer two of which are pertinent here. In the outermost layer is the trapezius muscle 48 which covers the upper back and part of the neck and shoulders. It has an elongated inner border that has an upper termination at the base of the skull and a lower termination down at the base of the dorsal vertebrae, and thus spans the length therebetween adjunct to all the cervical and dorsal vertebrae. From this inner border, the fibers of the trapezius muscle 48 converge as they extend outwardly, to converge on the inner margin of the scapula 20's spine 22 and acromion process 24. In the next layer are the rhomboid muscles 52, which extend in a flat band from an origin or inner border on the spinous process of generally the upper dorsal vertebrae, down and out to an outer extreme attached to the inner border of the scapula 20.

FIG. 4a shows that the muscles of the chest and shoulder area include the pectoral and the deltoid muscles 54, 56 and 58. The pectoralis major muscle 54 has a curved origin or inner border ranging from about the mid-point of the clavicle, and from there arcing in and down about as far as half-way down the sternum 60. The pectoralis major muscle 54 terminates in a flat tendon which is inserted into the humerus (see FIG. 2). The pectoralis minor muscle 56 (see FIG. 4b), which is covered by the pectoralis major muscle 54, terminates in a tendon attached to the coracoid process 42 of the scapula 20. The deltoid muscle 58, as shown by FIG. 4a, gives the rounded outline to the shoulder. Its name comes from its inverted-Δ shape. The deltoid muscle 58 has an extensive origin that arises from (i) the outer third of the clavicle 34, (ii) the acromion process 24 of the scapula 20, as well as from, (ii) the spine 22 of the scapula 20. From this extensive origin the fibers of the deltoid muscle 58 converge to form a tendon inserted in the shaft of the humerus.

FIG. 4b shows an inner layer of muscles of the chest, shoulder and arm area. The long tendon of the biceps attaches to the upper margin of the glenoid cavity 36 of the scapula 20. The short tendon attaches to the coracoid process 42. The serratus anterior (also serratus magnus) muscle 62 originates on the vertebral or inner border of the scapula 20 (refer to FIG. 1), and from there hugs the rib cage to extend to an opposite end where it terminates in a series of fingers attached to the ribs. The subacromial bursa 64 (along with the rotator cuff, discussed below) occupies the interspace between the humeral head 38 and the acromion process 24, and facilitates gliding therebetween. The subscapularis muscle 66 has a diverse origin, but it primarily originates in the subscapular fossa of the scapula 20 (see reference numeral 68 in FIG. 2). From its diverse origin, the subscapularis muscle 66 converges into a tendon attached to the front of the humeral head 38.

FIG. 5 shows the outer extremes of each of the supraspinatus muscle 70, the infra-spinatus muscle 72, and the teres major and teres minor muscles 74 and 76. The outer extremes of each of these muscles attach to or around the humeral head 38. Three of these tendons, namely, the teres minor 76 and the supra- and infra-spinatus tendons 70 and 72, plus a fourth tendon, the subscapularis tendon 66 (see FIG. 4b), form what is more generally known in orthopedics and sports medicine as the rotator cuff.

The shoulder joint is capable of movement in every direction, namely, forwards (flexion) and backwards (extension), out and up from the side (abduction), and into the side (adduction), as well as rotation (spinning) inwards (internal rotation) and outwards (external rotation), plus circumduction (pivoting). The scapula 20 is capable of being moved upwards (elevation) and downwards (depression), forwards (protraction) and backwards (retraction), as well as circumduction (pivoting) from a given resting alignment out and up (lateral or upward rotation), or in and down (medial or downward rotation), over the back of the rib cage. The muscles which raise the scapula 20 include the upper fibers of the trapezius 48 and the two rhomboids 52; those which depress it include the lower fibers of the trapezius 48 and the pectoralis minor 56. The scapula 20 is drawn backwards by the rhomboids 52 and the middle and lower fibers of the trapezius 48, and forwards by the serratus anterior 62 and pectoralis minor 56, assisted by, when the arm is fixed, the pectoralis major 54. The literature indicates the average range for scapular elevation and depression is between 10 and 12 cm, the average amount of protraction and retraction is 15 cm, and the average range of circumduction (pivoting) is between opposite extremes about 60° apart. See, e.g., K. Andeway, "Scapular Malalignment in Upper Quadrant Dysfunction," in *PT Magazine,* July 1994, pp. 60–65.

There are various disorders or pathologies to the areas of the neck, the shoulder, the upper trunk as well as the temporo-mandibular joint (i.e., the jaw), the treatment of which can involve proper dynamic positioning of the posture and/or dynamic stabilization of the scapula, as will be more fully explained below. What is needed is an effective orthopedic garment for properly, dynamically positioning the posture and/or dynamically stabilizing the scapula, which garment can be dressed into by a patient, male or female, without outside or professional help (following, of course, an original fitting and course of instruction in the use of the garment), and which is multiply adjustable for comfort and/or special support, wearable under regular clothing, re-usable, economical, and non-allergenic to the skin of the patient.

SUMMARY OF THE INVENTION

Various objects and aspects in accordance with the invention are provided in an orthopedic base garment and strap system for treating an involved shoulder, upper trunk or quadrant pathology in a given patient.

The system includes an elastic base garment that has at least one upper arm encircling portion, a torso encircling portion, and an arm-and-shoulder portion spanning between and interconnecting the upper arm encircling and torso encircling portions. The base garment has diverse inner and outer surfaces such that the inner surface is adapted for high friction contact with the patient's skin or a thin undergarment worn by the patient, whereas the outer surface being provided with hook-fastener securing areas.

The torso encircling portion is configured as opposite belt straps, one of which belt straps has hook fasteners. That way, the belt straps allowing releasable formation of a belt around the patient's torso underneath and clear of the breasts.

The system includes not only the elastic base garment but also one or more auxiliary straps of assorted lengths and which have hook-fastener compatible ends for securing to the base garment in diverse arrangements. These straps are elastic in order to allow compression against the patient in order to sufficiently enhance dynamical positioning of the posture and/or dynamical stabilization of the scapula and the like.

By dynamically stabilizing or positioning the scapula, this can positively enhance or influence pathologies of the shoulder girdle area. What has previously been achieved by taping techniques can now be accomplished by an orthopedic garment and strap system in accordance with the invention. Its many benefits include the following.

It eliminates the skin irritation that repetitive daily taping can cause. It gives a patient greater freedom of travel and independence because the orthopedic garment allows the patient to independently dress him or herself and effectively treat his or her pathology.

Since the straps allow adjustment, the patient can change the amount of support or compression given by any strap as his or needs or discomfort changes during the day. The base garment is especially adapted for the large-breasted patient, male or female, because it allows clearance for large breasts without any compression against them whatsoever.

The garment further has an open arm pit or axilla to allow increased ventilation in that area and reduce discomfort due to the garment (or tape wrap) from insulating and/or warming up the patient too high.

A number of additional features and objects will be apparent in connection with the following discussion of preferred embodiments and examples.

BRIEF DESCRIPTION OF THE DRAWINGS

There are shown in the drawings certain exemplary embodiments of the invention as presently preferred. It should be understood that the invention is not limited to the embodiments disclosed as examples, and is capable of variation within the scope of the appended claims. In the drawings.

FIG. 3 is a rear perspective view of muscles of the back, wherein, on the left side is exposed the most exterior layer of muscles, and, on the right side, a first interior layer and parts of a second;

FIG. 5 is a rear perspective view of muscles of the shoulder and arm, the right side being broken away;

FIG. 8a is a front perspective view comparable to FIG. 7 except showing attachment of a trapezius strap to the base;

FIG. 8b is a rear perspective view thereof;

FIGS. 12a through 12d are a series of front perspective views that illustrate a given classification scheme of injuries to the acromio-clavicular articulation, wherein:

FIG. 12a shows a normal acromio-clavicular articulation,

FIG. 12b shows an acromio-clavicular articulation with sprained acromio-clavicular ligaments, and is classified a TYPE I injury, FIG. 12c shows an acromio-clavicular articulation with disrupted acromio-clavicular ligaments and sprained coraco-clavicular ligaments, and is classified a TYPE II injury, and, FIG. 12d shows an acromio-clavicular articulation with disrupted acromio-clavicular and coraco-clavicular ligaments, and is classified a TYPE III injury;

FIG. 13 is a perspective view of an alternate orthopedic garment in accordance with the invention for dynamically enhancing proper posture in the upper extremity;

FIG. 14a is a front perspective view of the FIG. 13 orthopedic garment as worn by a patient, whose outline is shown dashed lines, wherein an auxiliary strap is shown with one end attached to the right shoulder of the garment on the patient;

FIG. 14b is a front perspective view comparable to FIG. 14a except showing the auxiliary strap with its opposite end attached to the garment under the left breast of the patient;

FIG. 14c is a front perspective view comparable to FIG. 14b except showing the completed attachment of a second auxiliary strap in mirror opposite relation to the first strap;

FIG. 15a is a rear perspective view of FIG. 14a;

FIG. 16 is a front perspective view of still another embodiment of the orthopedic garment in accordance with the invention, for dynamic scapular stabilization and the like;

FIG. 17a is a front perspective view thereof as worn by a patient, whose outline is shown in dashed lines;

FIG. 17b is a rear perspective view thereof;

FIG. 18 is a front perspective view of opposite left and right versions of the base garment of FIG. 16 shown worn by one patient at the same time in order to obtain the equivalence of a bilateral garment;

FIG. 19a is a front perspective view comparable to FIG. 17a except showing attachment of an deltoid strap to the base;

FIG. 19b is a rear perspective view thereof;

FIG. 20a is a front perspective view comparable to FIG. 19a except showing attachment of a coraco-clavicular strap to the base and over the deltoid strap;

FIG. 20b is a rear perspective view thereof;

FIG. 21a is a front perspective view comparable to FIG. 20a except showing attachment of an acromio-clavicular strap to the base and over the coraco-clavicular and deltoid straps;

FIG. 21b is a rear perspective view thereof;

FIG. 22a is a front perspective view comparable to FIG. 17a except showing attachment of a bifurcated strap to the base;

FIG. 22b is a rear perspective view thereof;

FIG. 23a is a front perspective view comparable to FIG. 22a except showing an alternate attachment arrangement of the bifurcated strap to the base;

FIG. 23b is a rear perspective view thereof;

FIG. 24a is a front perspective view comparable to FIG. 17a except showing attachment of a trapezius strap to the base;

FIG. 24b is a rear perspective view thereof;

FIG. 25 is a rear perspective view comparable to FIG. 24b except showing attachment of the coraco-clavicular strap simultaneously to the base and trapezius strap; and, FIG. 26a is a front perspective view comparable to FIG. 17a except showing attachment of a rhomboid strap to the base; FIG. 26b is a rear perspective view thereof; and, FIG. 26c is a side perspective view thereof.

DETAILED DESCRIPTION OF THE INVENTION

Figure 6:
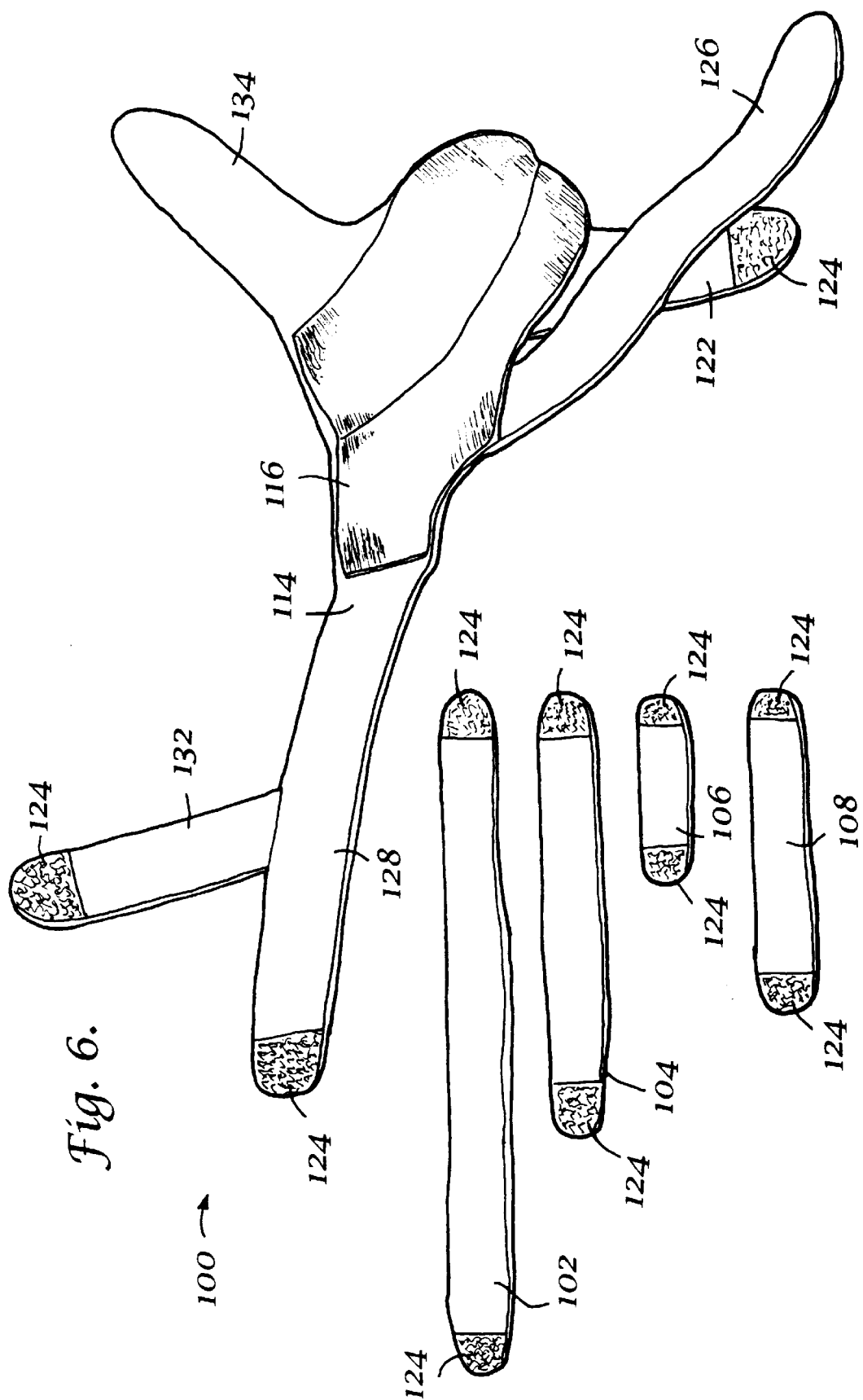
FIG. 6 is a perspective view of an orthopedic garment in accordance with the invention for dynamic scapular stabilization.

In FIG. 6, an orthopedic garment 100 in accordance with the invention for dynamic scapula stabilization is stretched out as generally resting flat on a given horizontal surface (not shown). Along with the garment 100 are shown several auxiliary straps 102, 104 and 106 for enhancing the effectiveness of the garment 100. The orthopedic garment 100 has an outer surface 112 (see FIG. 7) and an inner surface 114 opposite to the outer surface 112. As shown by FIG. 6, the orthopedic garment 100 is resting with its outer surface 112 down and its inner surface 114 up.

Figure 7:
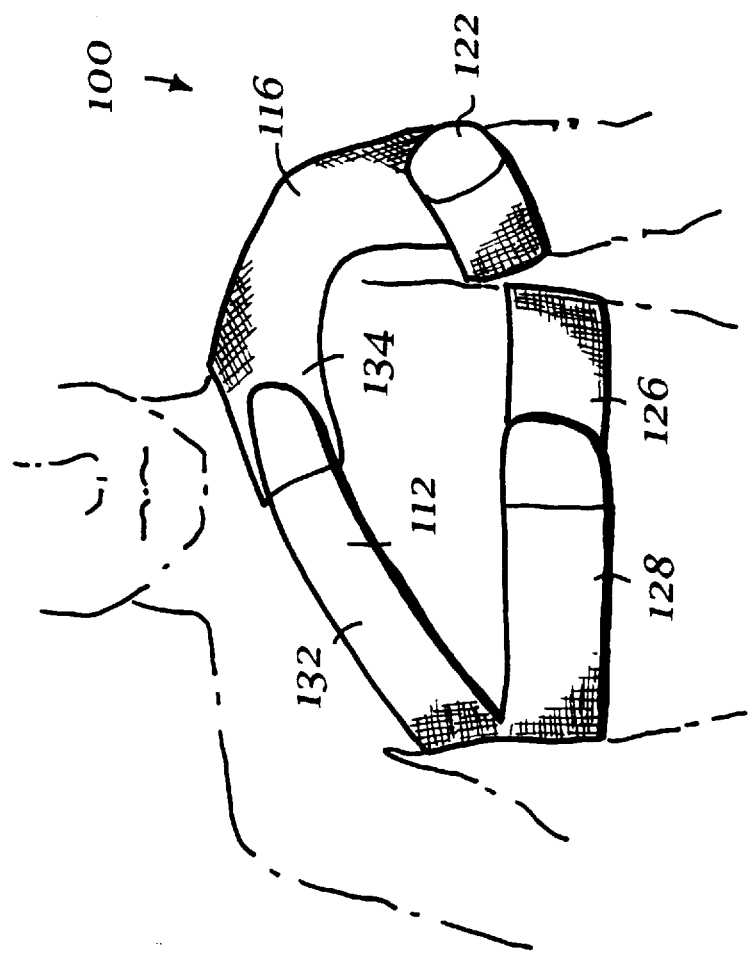
FIG. 7 is a front perspective view thereof as worn by a patient, whose outline is shown in dashed lines.

The material used in the orthopedic garment 100 includes a neoprene or like resilient material that forms a core which is covered by an inner liner that defines inner surface 114 (i.e., inner relative to the inner surface) and an outer liner that defines outer surface 112 (see FIG. 7). The inner liner which defines inner surface 114 can be Terry™ cloth or a like material which is comfortable to the skin yet absorbs perspiration, allows the skin to ventilate, and thereby minimizes trapping dampness against the skin. The outer liner which defines outer surface 112 (FIG. 7) is made of a nylon weave or the like that is Velcro™ compatible, i.e., it forms a pile for closure with hook material of a hook-and-pile fastening system (e.g., Velcro™).

Parts of the inner liner (which defines inner surface 114) are covered by chamois or a like material in the portions 116 of the garment that rest against the outer arm and the top of shoulder, including the scapula. The chamois 116 or the like is chosen for its ability to frictionally grab the skin of the patient and minimize or eliminate slipping therebetween, but also be comfortable and non-allergenic to the skin of the patient.

The orthopedic garment 100 shown by FIG. 6 is arranged and configured for treating pathologies of the left shoulder. It could be alternatively arranged in a mirror opposite version for a right shoulder. It also could be arranged for bilateral treatment of the left and right shoulders concurrently. Accordingly, terms like "left" and "right" are used merely for convenience in this description and do not limit the invention to the particular arrangement shown in the drawings.

The shape and arrangement of the orthopedic garment 100 includes the arm and shoulder portion 116 which, as mentioned above, is covered on the inner surface with chamois or a like non-slip material for frictionally grabbing the skin of the patient. The garment also includes an arm strap 122 which terminates in a patch 124 of hook material for closure with the outer liner (which defines outer surface 112) of the arm and shoulder portion 116 in order to form a sleeve, as shown by FIG. 7. The garment 100 further includes a pair of generally opposite chest straps 126 and 128 extending from a generally common root in the arm and shoulder portion 116, to extend in opposite directions therefrom and meet each other in the front of the chest of the patient (see FIG. 7) as a belt worn around the chest under or below the breasts. The right (i.e., the patient's or wearer's right) chest strap 128 includes a fork 132 which, when the right chest strap 128 is wrapped around the patient, diverges from the right chest strap 128 approximately under the right or non-involved arm pit of the patient. The fork strap 132 extends therefrom diagonally upwards above the breast and across the front of the chest of the patient to meet a down flap 134 that extends diagonally down to the fork strap 132 from the arm and shoulder portion 116 of the garment, as shown by FIG. 7. FIG. 6 also shows the arrangement and location of various patches 124 of hook material on the garment 100's inner surface 114.

In use, the orthopedic garment 100 is worn by the patient as shown by FIG. 7. The arm strap 122 forms a loop with the arm and shoulder portion 116 to define a sleeve, and is worn on the involved arm (i.e., the left arm here, or whichever side of the patient that has the given pathology). The opposite chest straps 126 and 128 form a loop or belt around the chest of the patient and fasten together approximately in the middle of the front of the chest below the breasts. The fork strap 132 extends diagonally up to the down flap 134 of the arm and shoulder portion 116, and the fork strap 132 and down flap 134 likewise fasten together approximately in the middle of the front of the chest above the breasts. It is an inventive aspect of the garment 100 that the various straps diverge above or below the breasts of the patient so that the garment is as comfortable for use by female or heavy-breasted patients (male or female) as well as by flat-chested patients.

Another inventive aspect of the orthopedic garment 100 relates to its configuration and arrangement so that the patient can preferably dress into the orthopedic garment 100 alone, by him or herself without professional or outside help, even with an immobile left arm. The steps that the patient should take to do this are preferably the following.

First, the patient should form the sleeve via the arm strap 122 and the arm and shoulder portion 116. If the patient is not too immobile, he or she might be capable of doing this directly on his or her arm. Alternatively, if the patient is too stiff or immobile to do that, the patient could build the sleeve before-hand, and then slip his or her left arm into the pre-built sleeve. By whichever way the patient gets his or her arm into the sleeve, the patient follows that with forming the chest loop or belt via the opposite chest straps 126 and 128. Finally, the patient should secure the fork strap 132 with the down flap 134. These last two steps require an act of fastening that occurs in the front of the chest of the patient, which can be accomplished even by a patient with an immobile left arm.

FIGS. 8a though 11b show the attachment and arrangement of the different auxiliary straps 102, 104, and 106. The material used to make these straps is neoprene or a like resilient material, with hook patches 124 affixed at the opposite ends thereof (see FIG. 6). The longest strap 102 (FIGS. 8a and 8b) is approximately 28 inches (70 cm) long, the shortest strap 106 (FIGS. 10a and 10b) is about 8 inches (20 cm) long, and the mid-sized straps 104 and 108 (FIGS. 9a/9b and 11a/11b, respectively) are around 18 inches (45 cm) long and 10 inches (25 cm), respectively.

In FIGS. 8a and 8b, this strap 102 is referred to as a trapezius strap because clinical evidence suggests that it enhances the positioning of and pull on the scapula ordinarily achieved by the middle and lower fibers of a healthy trapezius muscle 48 (see, e.g., FIG. 3). The trapezius strap 102, like the orthopedic garment 100 generally and like the other two straps 104 and 106 as well, preferably can be affixed and adjusted to comfort by the patient alone, without outside help. To do this, the patient attaches one end of the strap 102 to the outer liner (which defines outer surface 112) of the orthopedic garment 100 on the front of the shoulder as shown in FIG. 8a. In fact, the preferred location is approximately on the front of the acromion process of the scapula. From this origin, the trapezius strap 102 is looped behind the back of the patient and under the uninvolved arm pit to be secured to the chest strap(s) 126/128 of the orthopedic garment as shown in FIG. 8a. FIG. 8b shows how the trapezius strap 102 is arranged across the back. The end of the trapezius strap 102 that attaches to the chest strap(s) 126/128 is tightened or loosened as desired by trial and error until a comfortable or supportive fit is achieved.

Figure 9B:
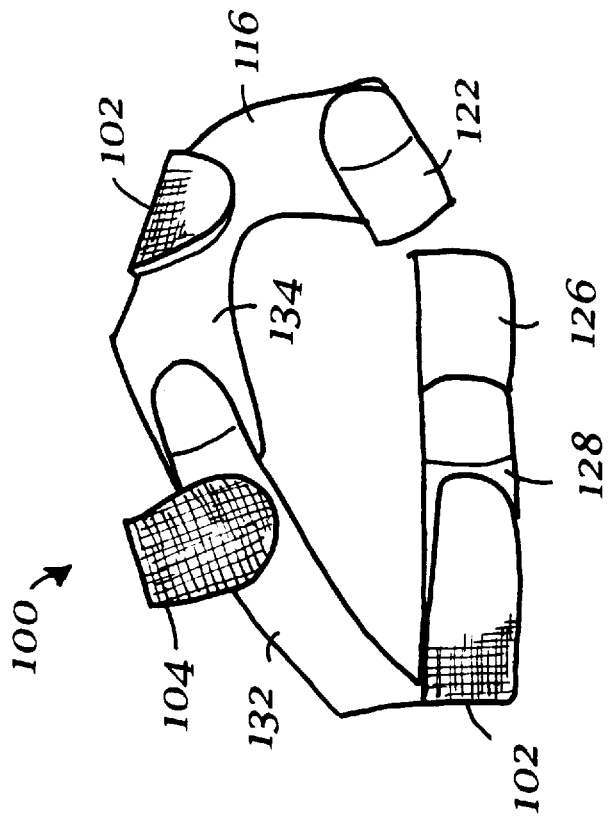
FIG. 9b is a front perspective view thereof.
Figure 9A:
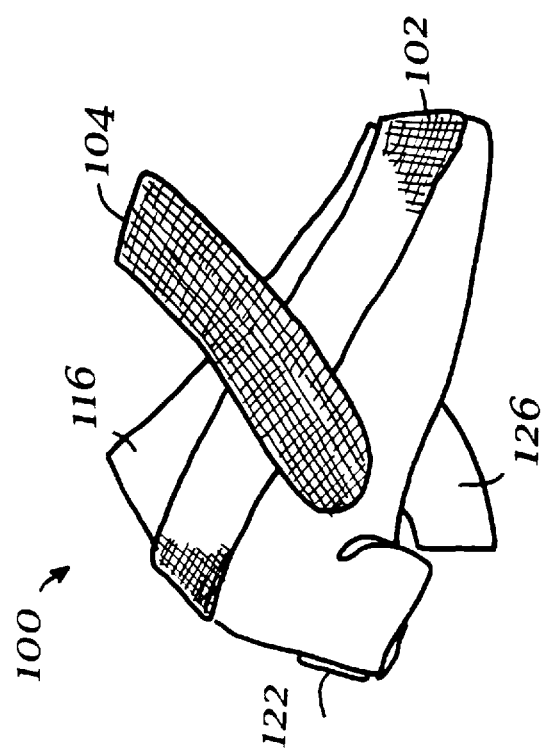
FIG. 9a is a rear perspective view comparable to FIG. 8b except showing attachment of a rhomboid strap to the base.

In FIGS. 9a and 9b, this strap 104 is labeled the rhomboid strap because clinical evidence suggests that it enhances the positioning of and pull on the scapula ordinarily achieved by healthy rhomboid muscles (see, e.g., FIG. 3). The patient first attaches one end of the rhomboid strap 104 on his or her back, at a position over the lower outer margin of the scapula in the rest position for an erect standing posture, with arms down. From this point of origin, the opposite end of the rhomboid strap 104 is pulled over and across the crotch of the neck and shoulder on the uninvolved side, to be attached to the diagonal band formed by the fork strap and down flap 132 and 134 of the garment 100. The rhomboid strap 104 is likewise attachable and re-attachable in the front of the chest of the patient until fitted as desired.

Figure 2:
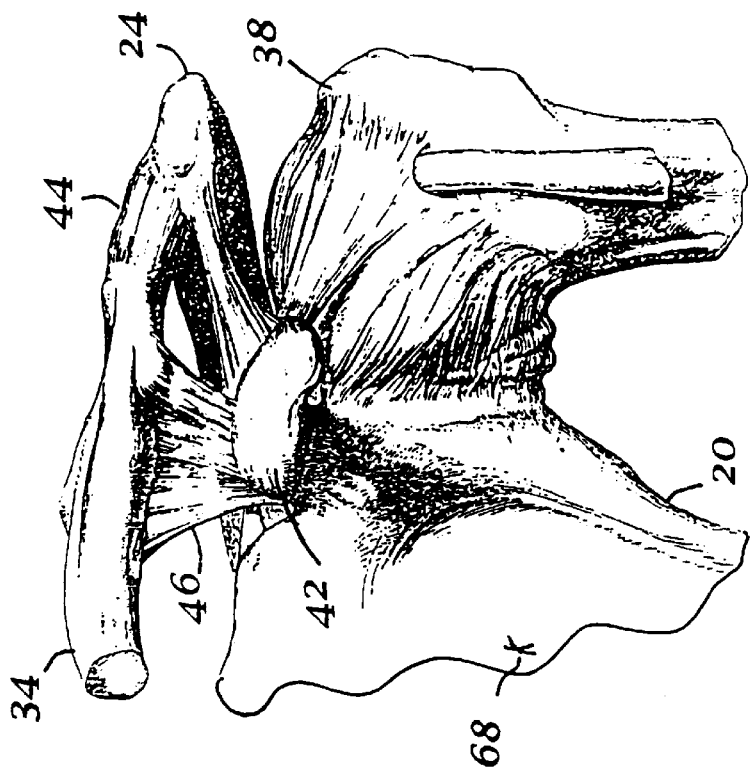
FIG. 2 is a front perspective view of the upper extremity of the human body, with the right side and portions of the left arm being broken away.
Figure 1:
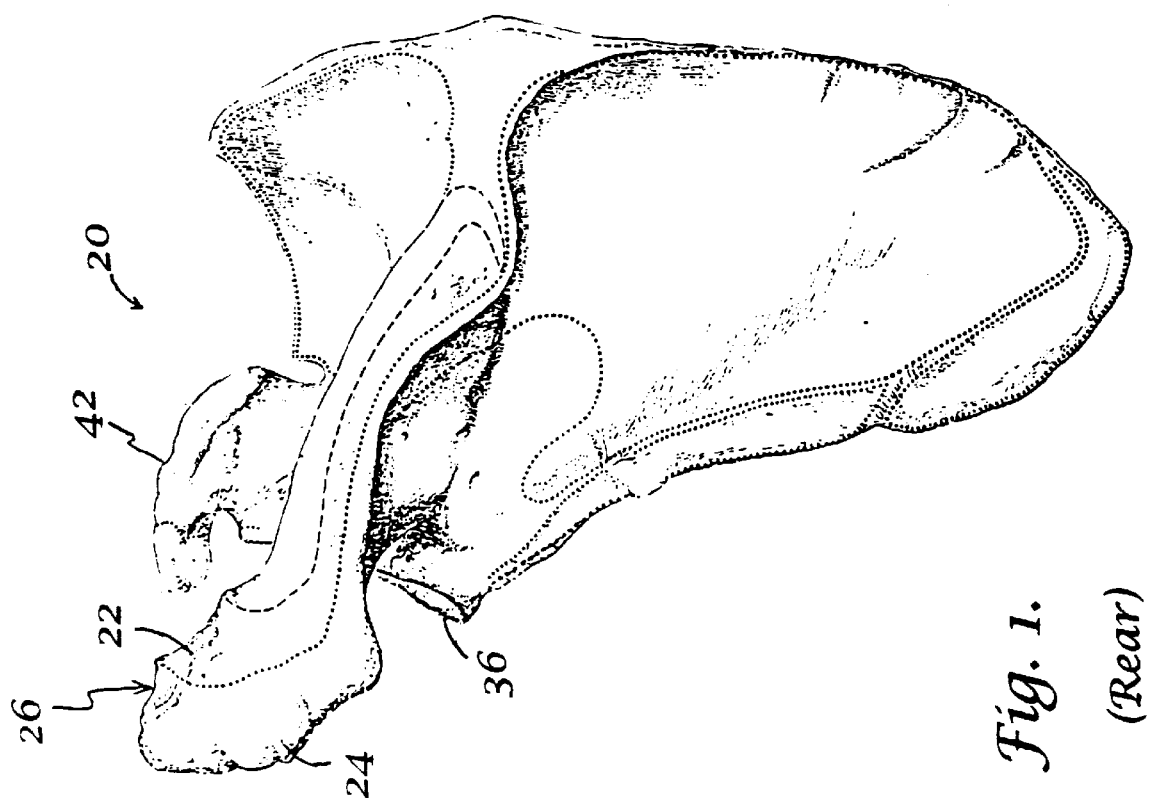
FIG. 1 is a rear perspective view of a left-side human shoulder blade:—scapula bone.
Figure 10B:
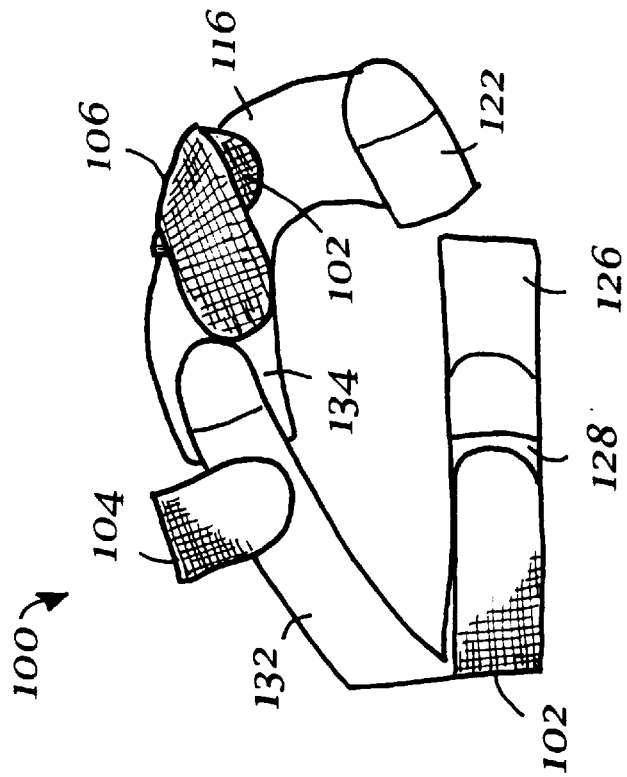
FIG. 10b is a front perspective view thereof.
Figure 10A:
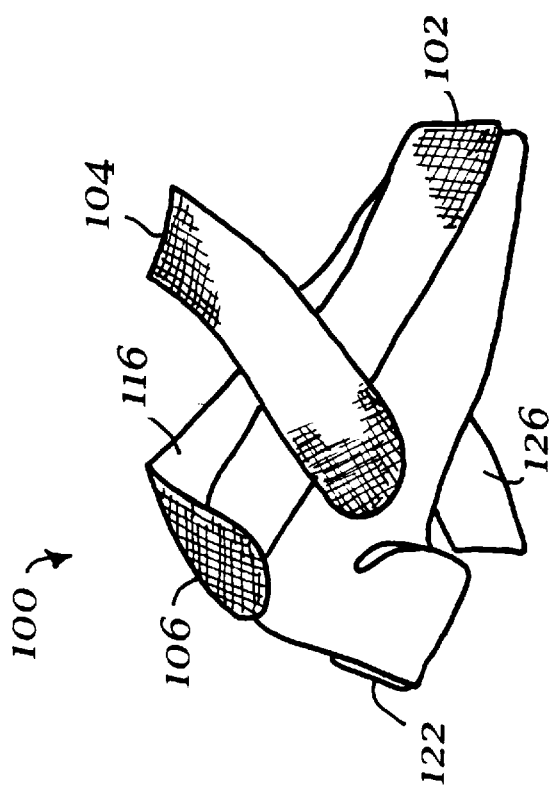
FIG. 10a is a rear perspective view comparable to FIG. 9a except showing attachment of an acromio-clavicular strap to the base.

FIGS. 10a and 10b shows strap 106. The strap 106 is labeled the acromio-clavicular strap because clinical evidence suggests that it enhances the positioning and coming together of the acromio-clavicular articulation that would ordinarily be achieved by healthy acromio-clavicular ligaments 44 (see, e.g., FIG. 2). The patient attaches this strap 106 preferably by securing the outer attachment point first, which is approximately behind the acromion process, or, more particularly, at the lower outer border of the rear of the acromion process. From this point of origin, the opposite end of the acromio-clavicular strap 106 is pulled in toward the patient's throat, crossing forwardly over the clavicle, to attach to the down flap 134 about in the middle of the front of the clavicle as shown by FIG. 10b. This strap 106 is also adjustable as desired.

Figure 11B:
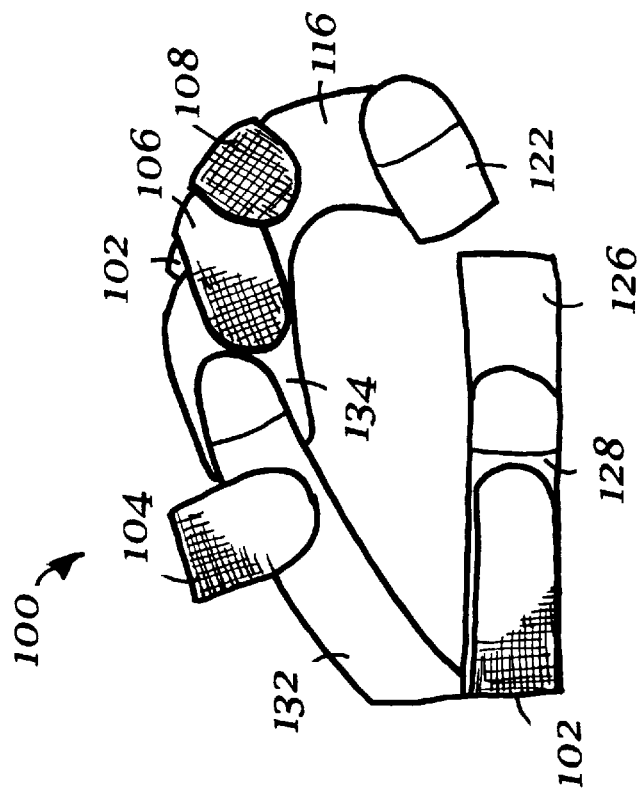
FIG. 11b is a front perspective view thereof.
Figure 11A:
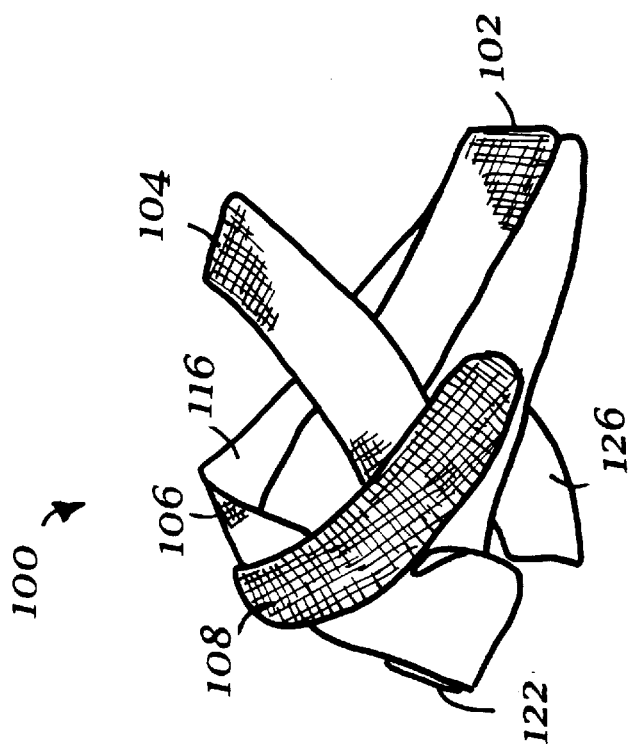
FIG. 11a is a rear perspective view comparable to FIG. 10a except showing attachment of a coraco-clavicular strap to the base.

FIGS. 11a and 11b shows strap 108. The strap 108, when used with the acromio-clavicular strap 106, extends overlying strap 106. This strap 108 is labeled the coraco-clavicular strap because clinical evidence suggests that, given a patient with separation of the acromio-clavicular joint (see, e.g., reference numeral 44 in FIG. 12c), strap 108 enhances the positioning and coming together of the coraco-clavicular as well as acromio-clavicular ligaments 44 and 46 that would ordinarily be achieved by healthy acromio-clavicular and coraco-clavicular ligaments 44 and 46 (see, e.g., FIG. 2). The patient attaches this strap 108 preferably by securing the outer attachment point first, at the lower inner border of the scapula (see FIG. 11a). From this point of origin, the opposite end of the coraco-clavicular strap 108 is pulled in over the same-side shoulder (i.e., the left shoulder in the drawings) crossing forwardly over the top of the shoulder, to attach to the down flap 134 about in the middle of the front of the acromion process, as shown by FIG. 11b. This strap 108 is also adjustable as desired, and it most significantly gives the scapula upward and lateral support when the acromio-clavicular ligaments 44 have separated, and thus counteracts a drop in the elevation of the scapula, and subsequent medial/downward rotation, due to gravity combined with absence of support from the acromio-clavicular ligaments 44.

Given the foregoing, the orthopedic garment 100 in accordance with the invention is useful for dynamic scapular stabilization by improving the biomechanics of the scapula, and hence the whole shoulder girdle, by promoting proper scapular positioning and movement mechanics as the scapula is moved through its motions. Other advantages include the following. The garment 100 naturally enough promotes the proper resting alignment of the scapula. It enhances proper positioning and gliding of the humeral head (ball) in the scapula's glenoid cavity (socket). It gives additional support to the muscles connected to and responsible for moving the scapula, and thereby (i) relieves tension in those muscles as well as (ii) obviates compensation from accessory muscles and thus prevents secondary pathologies or muscle strains as resultant from the base or primary pathology.

A given patient has a need for dynamic scapular stabilization when he or she suffers from a diverse variety of shoulder, neck and arm pathologies, including without limitation the following kinds:—namely, (i) acromio-clavicular strains, (ii) various impingement syndromes, (iii) thoracic outlet syndromes, and, (iv) the "winged" scapula condition.

Figure 12A:
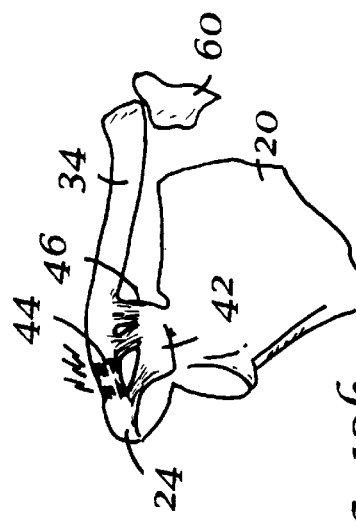
Figure 12B:
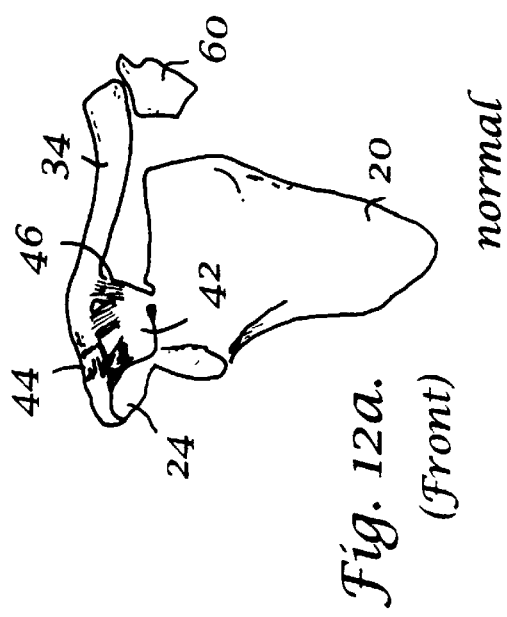
Figure 12C:
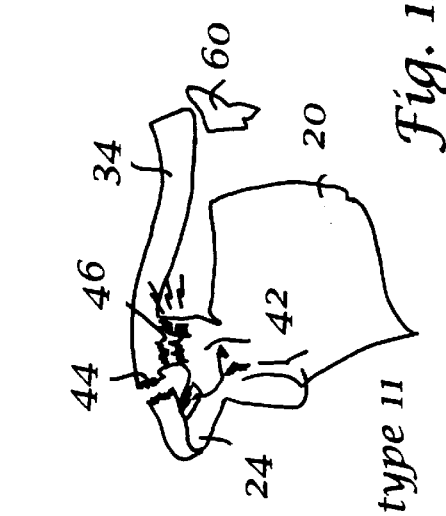

Acromio-clavicular strains and separations are shown in FIGS. 12a through 12d. FIG. 12a shows a normal joint. FIG. 12b shows an injury that resulted from a mild force to the point of the shoulder, which produced a minor strain to the fibers of the acromio-clavicular ligaments 44. This injury is a TYPE I injury. The acromio-clavicular ligaments 44 remain intact, and the acromio-clavicular joint remains stable. FIG. 12c shows a TYPE II injury. A moderate force to the point of the shoulder is severe enough to rupture the acromio-clavicular ligaments 44. The outer extremity of the clavicle 34 is unstable because the scapula 20 is attached to the clavicle 34 only by the coraco-clavicular ligament 46. The scapula 20 may adversely rotate inwardly (counterclockwise in FIG. 12c) and thereby widen the acromio-clavicular joint 44. The scapula 20 might also shift slightly downwards relative to the outer extremity of the clavicle 34. There may be minor stretching to the coraco-clavicular ligament 46.

Figure 12D:
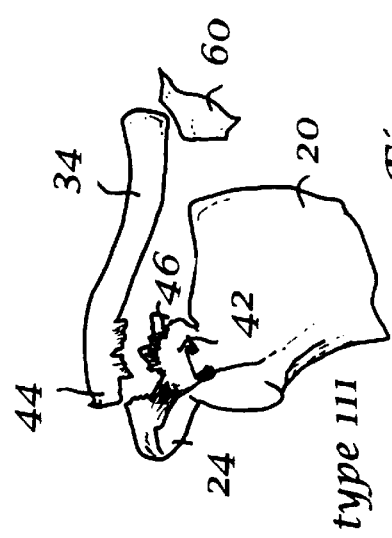

FIG. 12d shows a TYPE III injury. A severe force to the point of the shoulder has disrupted the acromio-clavicular and coraco-clavicular ligaments 44 and 46. The distal end of the clavicle 34 appears to have sprung up as a sprung piano key or the like. Appearances aside, the actual deformity is truly the downward displacement of the scapula 20 and entire upper extremity relative to the generally stationary clavicle 34. The deltoid and trapezius (not shown) are likely disrupted from the outer extremity of the clavicle 34 also.

The orthopedic garment 100 in accordance with the invention is ideally suited for treatment of TYPE II injuries above, in assisting closing the interspace between the clavicle 34's outer extremity and the acromion process 24. The garment 100 would be effective in treating a TYPE I injury if not overly so because this injury might not require as much external support as given by the garment 100. A TYPE III injury most often initially requires surgical correction and/or more aggressive support of the entire arm, such as a sling or like support, after which, during recovery and rehabilitation, the garment 100 in accordance with the invention would be highly effective in the rehabilitation thereof.

Figure 4B:
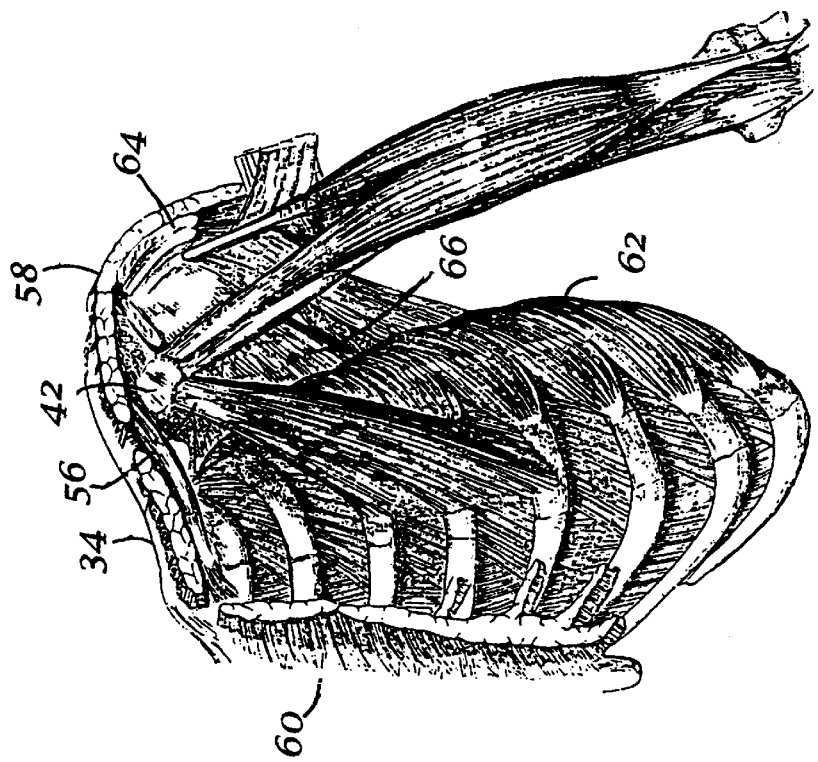
FIG. 4b is a front perspective view of interior muscles of the chest and shoulder, the right side being broken away.
Figure 4A:
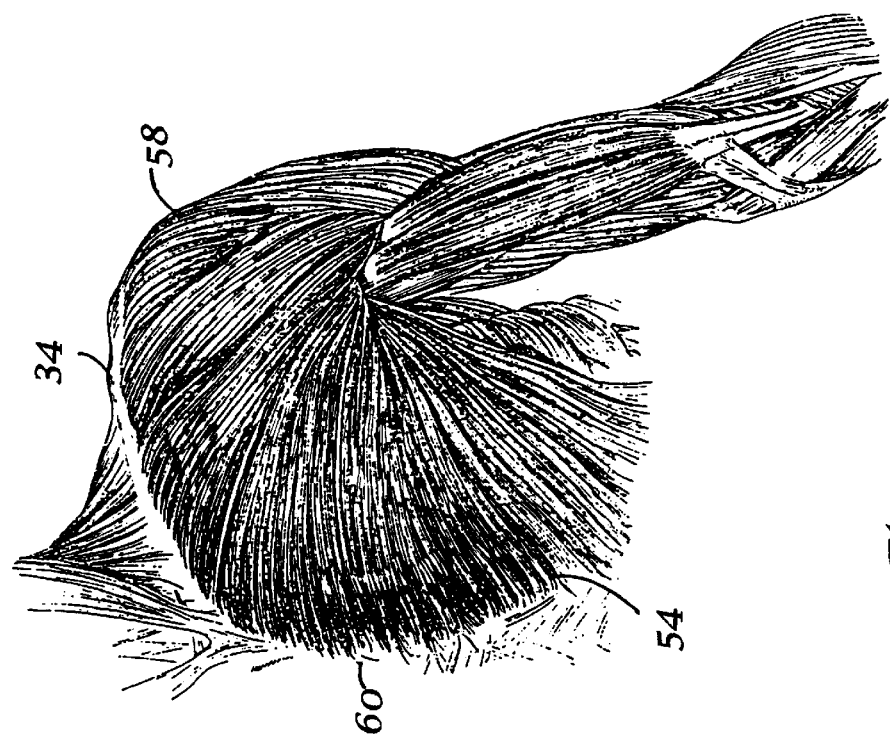
FIG. 4a is a front perspective view of the most exterior layer muscles of the chest and shoulder, the right side being broken away.

Impingement syndrome injuries commonly occur in, but by no means limited to, athletes. Impingement syndrome injuries in the shoulder and arm area include, rotator cuff tendinitis, and, subacromial bursitis. With reference to FIG. 4b, subacromial bursitis is inflammation of the bursal sac and membrane 64 positioned directly below the acromion process 24 of the scapula 20 (compare, e.g., FIG. 2). A typical cause of this inflammation is due to the abnormal constriction of the interspace between the acromion process 24 and the humeral head 38. When that happens, the subacromial bursa 64 can become "pinched" or compressed, and sorely inflame as a result. The garment 100 in accordance with the invention is effective for maintaining proper relative positioning, or "centralization" (i.e., a term of art), between the humeral head 38 and glenoid cavity 36 of the scapula 20, and likewise the humeral head 38 and acromion process 24.

To turn to FIGS. 4b and 5, rotator cuff tendinitis involves inflammation of the any of the four tendons that constitute the rotator cuff, which are, as previously stated, the teres minor tendon 76, the supra- and infra-spinatus tendons 70 and 72, and the subscapularis tendon 66. Sports medicine data shows that rotator cuff injuries most commonly involve pinching of or inflammation in the supra- and infra-spinatus tendons 70 and 72, less commonly so in the subscapularis tendon 66, and only rarely in the teres minor tendon 76. The garment 100 in accordance with the invention is effective in enhancing the proper biomechanics of the shoulder for treatment of rotator cuff tendinitis. Also, the garment 100 is effective for rehabilitation following surgery to repair rotator cuff tears.

The thoracic outlet syndrome can be caused by, among other things, a drooping shoulder girdle. The nerve bundles that extend into the arm, as well as the artery and vein that supply and vent the arm, pass closely underneath the clavicle en route across the arm pit to the arm. Thoracic outlet syndrome is characterized by compression of these nerve bundles and/or arterial vessel, say, in the clavicular area, which manifests as pain in the arms, prickling in the fingers, weakness and wasting of the small muscles in the hand, and so on. Such compression, needless to say, is caused by improper alignment or positioning of an abutting or adjacent structure to the compressed nerve bundles or arteries. If this occurs in an improperly drooping shoulder girdle, which in any given case it may, then the orthopedic garment 100 in accordance with the invention is effective in supporting and dynamically stabilizing the shoulder girdle for proper positioning and biomechanics.

The "winged" scapula condition may be a special case of the thoracic outlet syndrome, or trauma or disease. Here, a nerve, called the long thoracic nerve, can be compressed, injured, or compromised, which results in partial or complete paralysis of the serratus anterior, and hence further results in the scapula sticking out and giving the appearance of a "wing." The garment 100 is effective in restoring proper alignment in a winged scapula.

The scapular/AC stabilizer can also be utilized in conduction with a generic arm sling/support when more aggressive support or unloading is desired in conjunction with the benefits of scapular control support as already described. For example, neurological insults such as cerebral vascular accident (CVA) or stroke, or more severe Grade III AC separations.

Among the above-described disorders, generally speaking, the longer or more chronic thee condition/disorder/dysfunction, the longer and more difficult it is to properly rehabilitate. It is the clavicular-type of trauma (e.g., motor vehicle accident with the shoulder harness portion of the seat belt) involving any or all of the acromio-clavicular, coraco-clavicular, and/or the sterno-clavicular joints/ligaments, that characteristically results in significant soft tissue trauma throughout the shoulder girdle. The clavicular-type of trauma is frequently accompanied by or associated with neck injuries too, and so can develop into thoracic outlet symptoms, which are the most enduring and require relatively long-lasting treatment programs.

The orthopedic garment 100 in accordance with the invention is a highly practical adjunctive measure for treating the already described disorders of the shoulder girdle, whether of a fairly recent onset or whether of a more chronic condition. As a result, the patient's symptoms are more easily managed not only in the clinic but also at home throughout the day, thereby facilitating improved function and independence. With symptoms more manageable, and proper biomechanics restored or enhanced, the professional physical rehabilitation specialist—physical therapist—now has an improved opportunity to more effectively rehabilitate the shoulder girdle through a method of proper training of the involved muscle groups in conjunction with the garment 100, and eventually eliminate the need for further use of the garment 100.

In addition, the cost in material and professional time of frequently-applied adhesive tape wraps and the like is eliminated since the patient is able to dress him or herself into and out of the garment without outside help. The garment 100 is comfortable to the skin and thus can be worn for indefinitely long periods of time discreetly under normal clothing without irritating or raising a rash in the skin, which frequently occurs with taping and the like. In view of the foregoing, the garment 100 is highly economical.

The orthopedic garment 100 also enhances smooth and coordinated motor control apparently by virtue that it closely surrounds and compresses comfortably against the skin and muscle of the patient. In more difficult language, the garment 100 gives the patient appropriate, tactile, proprioceptive input. To understand this better involves a brief explanation of the motor control functions of the nervous system.

In the performance of smooth and coordinated motor tasks—whereas there is no doubt that the signals sent to the muscles which energize movement are important—there is an important unconscious "feedback" signal which is sent from the muscles, which feedback signal conveys information regarding the position and movement of the muscles and joints. The nerves that are embedded in the muscles, the tendons and the joint capsules, which give these signals, are called proprioceptors. These feedback signals from the proprioceptors arc known to be important to smooth and coordinated muscle control.

When there is injury or inflammation to the tissue surrounding a given proprioceptor, it disturbs proper signal generation by the proprioceptor and, as a result, faulty mechanics in muscle control occur. It has been found that by wearing the garment 100 a patient improves and/or restores smooth and coordinated muscle control. This result is attributed to several factors, but among those factors, it is partly attributed to the garment 100 providing appropriate tactile proprioceptive input. Put differently, the compression or support (i.e., tactile input) that the garment 100 gives to the offended tissue appears to stimulate or enhance more proper proprioceptive signal generation. With a proper feedback signal apparently restored, smooth and coordinated motor control returns.

FIG. 13 shows an alternate orthopedic garment 200 in accordance with the invention for dynamically enhancing proper posture in the upper extremity. The orthopedic garment 200 includes left and right base portions 202 and 204 shown resting flat on a given horizontal surface (not shown), and beside the base portions 202 and 204 are a pair auxiliary straps 206. The base portions and straps 202, 204 and 206 have respective outer surfaces (sec FIG. 14a) and inner surfaces opposite the outer surfaces. In FIG. 13, the outer surfaces are down and the inner surfaces are up. The FIG. 13 base portions and straps 202, 204 and 206 are made from comparable materials as previously described above in connection with the FIG. 6 garment and straps 100, 102, 104 and 106. Thus the FIG. 13 base portions and straps 202, 204 and 206 comparably include arm and shoulder portions 212 made of chamois or a suitable substitute (as explained previously), as well as patches of hook and pile material 216 and 218. The hook and pile patches 216 and 218, however, insofar as the base portions 202 and 204 are concerned, are arranged differently relative to the FIG. 6 garment 100, as will be explained next. These differences could be incorporated in the FIG. 6 garment 100 if desired to give the FIG. 6 garment 100 the same advantages.

The left base portion 202 is worn by the patient over his or her left shoulder (see FIG. 14a), and appears on the right side of the view of FIG. 13. Each of the left and right base portions 202 and 204 has an arm strap 214. Each arm strap 214 has a patch of pile material 218 on the inner side thereof, which distinguishes the FIG. 13 arm straps 214 with the FIG. 6 arm strap 122. In FIG. 6, the arm strap 122 has a patch of hook material sewn to the inner side. For the FIG. 13 arm straps 214, the corresponding patches of hook material 220 are on the outside of the liner, and are shown in dashed lines. Either way (i.e., either FIG. 6 or 13), the arm straps 214 (or 122) are adjustable for forming sleeves to wear around a patient's arm above the elbow. However, placing the hook patch 220 on the outside of the garment 200, as shown by FIG. 13, keeps the hook material oriented away from the patient's skin. It is desirable if the hook patch 220 does not rest against the patient's skin while the left or right base portions 202 or 204 are worn because the hook material is known to irritate the skin.

The left and right base portions 202 and 204 have front straps 222 and 224, respectively, that extend diagonally across the front of the patient (i.e., across his or her chest) just above his or her breast (see FIG. 44a). As shown by FIG. 14a, either one of the front straps 222 or 224 does about the same work as three straps in the FIG. 6 garment 100: namely, the two opposing chest straps 126 and 128 as well as the fork strap 132. In comparison, the left front strap 222 (see FIG. 14a) is one piece relative to the opposing chest straps 126 and 128 (see FIG. 7) being two pieces, and the fork strap (FIG. 7) is omitted from the left front strap 222 (FIG. 14a).

Figure 15A:
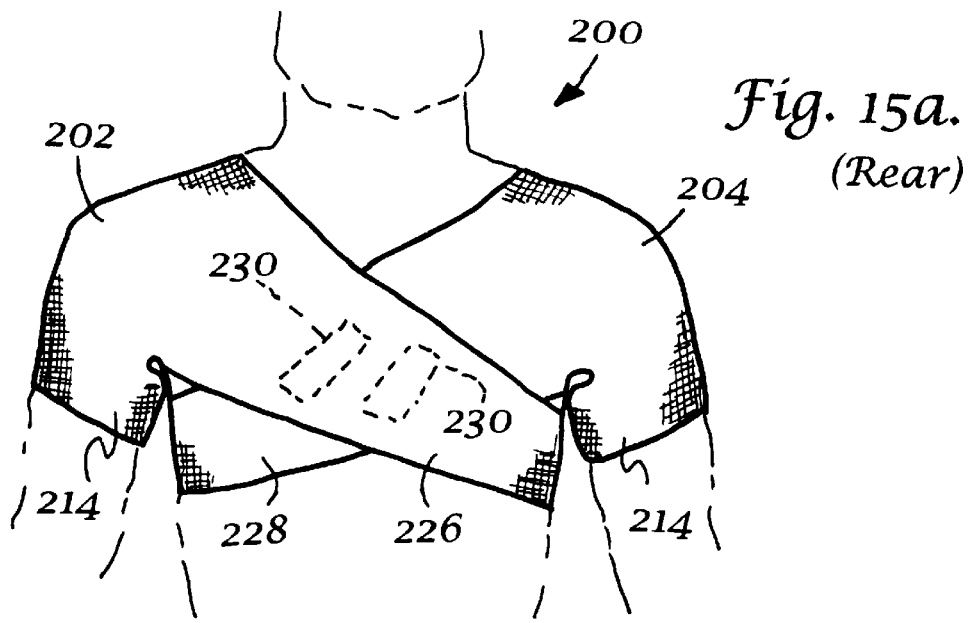

The left and right base portions 202 and 204 also have back straps 226 and 228, respectively, that extend diagonally across the patient's back (see FIG. 15a), which back straps 226 and 228 further extend under the opposite side arm pit (i.e., as again shown by FIG. 15a). FIG. 14a shows that the terminal end of the left side back strap 226 comes from underneath the patient's right arm pit to fasten together with the back strap 228 of the right base portion 204. FIG. 14a also shows that the back strap 228 of the right base portion 204 is looped around underneath the patient's left arm pit. The oppositely extending back straps 226 and 228 fasten together in front in the middle of the patient's chest for ease of convenience for the patient to attach by him or herself, without help from another person.

FIG. 13 shows that the back strap 228 of the right base portion 204 has a patch of hook material 216 near its terminal end, whereas the back strap 226 of the left base portion 202 does not. Only one of the two back straps 226 or 228 needs a patch of hook material, it being omitted from the other back strap 228 or 226 as redundant and needless.

FIG. 13 also shows that the front straps 222 and 224 have two patches 216 of hook material near their respective terminal ends. These two patches 216 allow adjustment for the size of the patient, whether if the patient has a relatively larger or smaller torso than another patient (these differences not shown). In use, the patient would determine which front strap hook patch he or she would use—based on trial and error—for comfort. After having made that determination, the patient would then cover the unused hook patch with a patch of pile material (not shown), which would rest against the patient's skin so that the patient would feel soft material as, for example, the inner liner of the base portions 202 or 204. That way, the unused hook patch 216 on the front strap 222 or 224 would be covered from irritating the patient's skin.

The left base portion 202 has affixed to the back strap 226 a pair of strips 230 of hook material, as near the arm and shoulder portion 212 as shown by FIG. 13. The use of these hook strips 230 is for fastening to the outer liner of the back strap 228 of the right base portion 204 (see FIG. 15a) as will be described below.

A patient, in order to dress him or herself into the left and right base portions 202 and 204, preferably does so by the following steps, as will be understood with general reference to FIGS. 14a and 15a. First the patient forms arm sleeves from the arm straps 214. Then he or she preferably inserts his or her right arm into the sleeve of the right base portion 204 (not illustrated), and following that he or she inserts his or her left arm into the sleeve of the left base portion 202. The order of dressing into the right base portion 204 before the left base portion 202, is preferred because, the back strap 226 of the left base portion 202 should preferably overlie the back strap 228 of the right base portion 204. That way, the hook strips 230 on the inside of the left back strap 226 are alignable to fasten to the outside of the back strap 228 of the right base portion 204, as shown by FIG. 15a.

An inventive aspect of the strips 230 of the hook material on the left back strap 226 is that, the relative crossing point of the left and right back straps 226 and 228 can be fixed before the patient begins to dress into the garment 200. Thus the patient need not have the help of another person to align the back straps 226 and 228 in a preferred alignment across his or her back. When the patient undresses out of the garment 200, he or she can leave the back straps 226 and 228 attached in any given position so that upon the next use, the back straps 226 and 228 are pre-positioned in the chosen given position.

The patient next grasps the terminal ends of the back straps 226 and 228—the left strap 226 in his or her right hand, the right strap 228 in the left hand—and fastens the back straps 226 and 228 together via the hook patch 216 on the right back strap 228 (compare FIGS. 13 and 14a). The back straps 226 and 228 are adjusted for comfort like a belt by trial and error.

At this point, the patient proceeds to attaching the front straps 222 and 224 in place. FIG. 14a shows the results of this. The patient pulls the terminal end of the right front strap 224 diagonally down to attach underneath his or her left arm pit to the back strap 228 of the base portion 204 it is common with:—namely, the right base portion 204. The same procedure is repeated with the left front strap 222 and left back strap 226. FIG. 14a shows the final results from the front of the patient after completion of dressing into the left and right base portions 202 and 204. FIG. 15a shows the final results from the rear.

FIGS. 14a through 15b show the attachment and arrangement of the auxiliary straps 206. In the drawings these straps 206 are shown the same size and attached symmetrically opposite to each other. However, this attachment arrangement is shown in the drawings merely for convenience in this description and does not limit the invention because it could be varied as desired for comfort and more effective posture support.

Figure 15B:
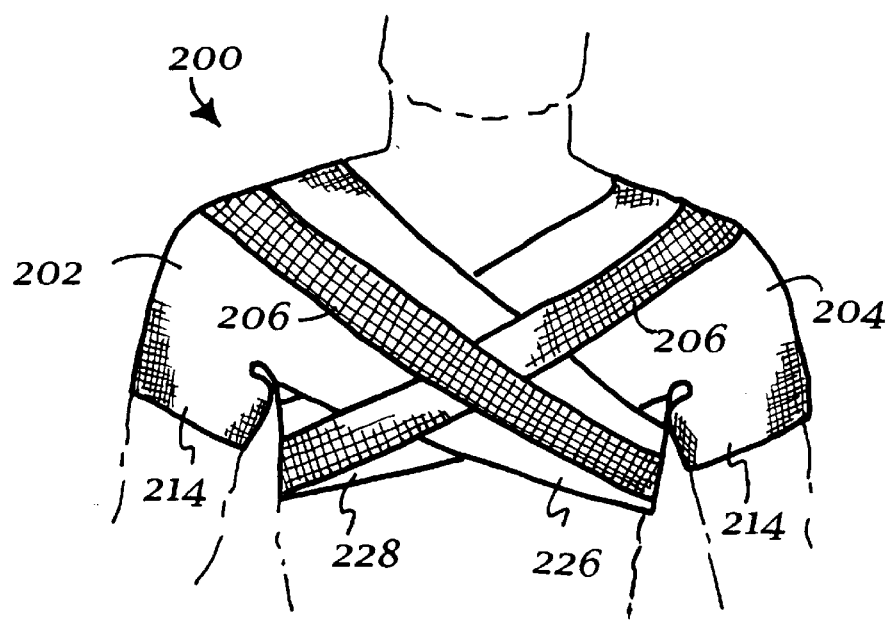
FIG. 15b is a rear perspective view of FIG. 14c.

Attachment of the right auxiliary strap 206 is shown in FIGS. 14a and 14b. It is called the right auxiliary strap because its point of origin begins on the front of the right shoulder, as shown by FIG. 14a. To start with, the patient attaches one end of the right auxiliary strap 206 to a point on the garment 200's right base portion 204 approximately on the front of the right shoulder, which is shown by FIG. 14a. The opposite end of the auxiliary strap 206, which is shown loose in FIG. 14a, is pulled around the patient's back to come out underneath his or her left arm pit, to attach to the fastened-together back straps 226 and 228 as shown by FIG. 14b. This process is repeated for the left auxiliary strap 206, and the results of this are shown by FIG. 14c. FIG. 15b shows FIG. 14c from the rear. A patient need not designate one or the other of the auxiliary straps 206 as left or right because the straps are generally interchangeable.

Given the foregoing, the FIGS. 14c and 15b orthopedic garment 200 in accordance with the invention is useful for promoting and/or enhancing proper posture with the shoulders relative the spine, and thereby is useful for treating various disorders, malalignments, and/or dysfunctions of the upper extremity.

More particularly, the purpose of the orthopedic garment 200 configured and arranged as shown by FIGS. 14c and 15b is to dynamically support and/or enhance proper posture in a given patient. There are various situations that exist where good posture is required for proper biomechanics and healing. One situation involves treatment of thoracic outlet syndrome, which has been described previously. Another situation involves thoracic compression fractures, the most common cause of which is the condition of osteoporosis typically limited to elderly patients, mostly women. And still another situation involves spine pathology, which includes treatment of cervical, lumbar and/or thoracic rib dysfunction. Spine pathology also includes treatment of dysfunctions in the temporo-mandibular joint, or, in more everyday language, the jaw.

The temporo-mandibular joint is involved with posture in the upper extremity because the muscles which move the jaw are also partly involved in maintaining correct posture of the jaw relative to the head and neck (the teeth and tongue also participate in this posture work, and nerve endings in the temporo-mandibular joint help guide the head and neck posture and level vision). Correspondingly, the posture of the head and neck affect the proper posture jaw. Put differently, before the posture of the jaw relative to the head and neck can be effectively treated, then preferably the head and neck are supported in a given proper posture.

Inventive aspects of the orthopedic garment 200 of FIGS. 14c and 15b include the following. Preferably the garment 200 can dressed into by the patient alone, without help from another person. Also, the garment 200 directly influences round shoulder posture because the base portions 202 and 204 directly encompass the patient's shoulders (FIGS. 14a through 15b), and, in combination therewith, the auxiliary straps 206 actively pull (or induce) the shoulders into (or to assume) a relatively more erect (or proper) posture. The base portions 202 and 204 may omit the arm and shoulder portions 212 (see FIG. 13, the omission of which is not shown) because there is less need for frictionally grabbing the skin for this garment 200 to effectively perform its posture supporting/enhancing work, as compared to the need for the FIG. 6 garment 100 to frictionally grab the skin as is important for dynamical scapular or acromio-clavicular stabilization.

Furthermore, the base portions 202 and 204 are configured such that, in combination with the arrangements of the auxiliary straps (FIGS. 14c and 15b), the patient is not gripped via a tightly encircled band of elastic material under the arm pit. This avoids compromising (or pinching or compressing) the neuro-vascular bundle under the arm pit. Thus the blood supply to the arm and hand should not be interfered with by the wearing of this orthopedic garment 200 in accordance with the invention.

Further still, the base portions 202 and 204 of the orthopedic garment 200 of FIGS. 14c and 15a are advantageously customizable to comfortably fit a given patient size, whether a relatively larger or smaller individual. Additionally, the auxiliary straps 206 dynamically enhance/support proper posture in accordance with a patient's needs. As a patient's day extends, the patient can loosen or tighten the auxiliary straps 206 in accordance with comfort or in accordance with periods of relative activity and inactivity. The auxiliary straps 206 give a patient the option of varying the point at which the auxiliary straps cross the patient's back (see FIG. 15b). If the auxiliary straps 206 are crossed at a relatively lower position on the spine, then such a crossing position allows the patient relatively more thoracic extension with scapular retraction, than otherwise. In contrast, if the auxiliary straps 206 are crossed at a relatively higher position on the spine (two different crossing points not shown), then such a higher crossing point enhances scapular retraction more than a lower crossing point.

FIG. 16 shows still another embodiment of the orthopedic garment in accordance with the invention including a base 300 and diverse auxiliary straps 302, 304, 306, 306', 308, and 310. Various portions of the base garment and straps have attached to them patches of hook material 324 of a hook-and-pile fastening system. The FIG. 16 garment 300 is shown resting flat with its outer surface down (not in view, but indicated as 312 in FIG. 17a) and its inner surface 314 up. The base garment 300 is made substantially from Fabri-Foam™ material. This material is breathable and allows ventilation to keep down discomfort due to perspiration. It is thin. It provides a skin-gripping, substantially non-migrating inner surface 314. Its exterior provides a Velcro™-attachable material so that the auxiliary straps can be attached about anywhere. The material is also sufficiently elastic to compress against the skin of or a thin undergarment on the patient to get a sufficient frictional grip on the patient to prevent unwanted migration.

The base garment 300 includes left and right chest (or waist or torso) straps 326 and 328 like those for the FIG. 6 garment 100. It also has a sleeve-forming arm strap 322 for encircling an upper arm of the patient. It further includes a forked down strap 332 which has a point of origin in an arm-and-shoulder portion 316, from which it terminates in a front branch 336 and side branch 338.

In use, the garment 300 is worn by the patient as shown by FIGS. 17a and 17b. The arm strap 322 forms a loop depending from the arm-and-shoulder portion 316 to define a sleeve, and is worn on the involved arm (i.e., the right arm here, or whichever side of the patient that has the given pathology). The opposite torso straps 326 and 328 form a loop or belt around the mid-riff of the patient and fasten together at one side approximately under the front part of the torso of the involved arm of the patient, and below the breasts. The forked down strap 332 extends down from the arm-and-shoulder portion 316 wherein the front and side branches 336 and 338 flank opposite sides of the right breast of the patient, to attach as shown to the band of the connected torso straps 326/328. It is an inventive aspect of the garment 300 that the various straps diverge above or below the breasts of the patient so that the garment is as comfortable for use by female or heavy-breasted patients (male or female) as well as by flat-chested patients.

FIG. 18 is a front perspective view of opposite left and right versions of the base garment 300 of FIG. 16 shown worn by one patient at the same time in order to obtain the equivalence of a bilateral base garment.

Still other inventive aspects of the orthopedic garment 300 relates to its configuration and arrangement so that a patient can preferably dress into it alone, so as not to require attendance by another to dress into it, even with an immobile right (or involved) arm. Preferably, the patient would first form the sleeve via the arm strap 322, but if the patient is not too immobile, he or she might be capable of doing this directly onto his or her arm. However, it still is preferred if the patient, on the supposition that he or she likely is too stiff or immobile to build the sleeve on his or her arm, would build the sleeve before-hand, and then slip his or her left arm into the pre-built sleeve. Irrespective how the patient gets his or her arm into the sleeve, the patient then forms the chest torso loop or belt via the opposite torso straps 326 and 328. Finally, the patient should secure the forked strap 332 as shown. The arm band 322 aside, the other straps fasten in the front of the patient's chest, which can be accomplished even by a patient who has an immobile left arm.

FIGS. 19a though 26c show the attachment and arrangement of the different auxiliary straps. These straps are neoprene or a like resilient material, with hook patches 324 affixed at the opposite ends thereof (see FIG. 16). The trapezius strap 302 is between approximately 18 to 36 inches (45 to 90 cm) long, the rhomboid strap 304 is between approximately 20 and 38 inches (50 to 95 cm) long, and the coraco-clavicular strap 308 is between approximately 8 and 13 inches (20 to 33 cm) long. Each of those straps is between about 2 and 3 inches (5 to 8 cm) wide. The shortest, or the acromio-clavicular strap 306 is about 3 to 6 inches (8 to 15 cm) long, and around 2 inches (5 cm) wide. The bifurcated strap 310 is about 20 to 40 inches (50 to 100 cm) long, and around 3 to 4 inches (8 to 10 cm) wide, which means that each branch 341 and 342 is about half that, or else between about 1.5 to 2 inches (4 to 5 cm) wide. The deltoid strap 306' is proportioned as follows:—it is between about 5 to 8 inches (13 to 20 cm) wide, and about 5 to 10 inches (13 to 25 cm) high. All the straps are labeled to allow the patient to choose them correctly from written and/or illustrated instructions.

FIGS. 19a and 19b show application of the deltoid strap 306'. Clinical evidence suggests that application of the deltoid strap 306' as shown promotes the proper resting alignment of the scapula and, as importantly, supports the upper arm by way of enhancing proper positioning and gliding of the humeral head (ball) in the scapula's glenoid cavity (socket). It gives additional support to the muscles connected to and responsible for moving the scapula, and thereby (i) relieves tension in those muscles as well as (ii) obviates compensation from accessory muscles and thus prevents secondary pathologies or muscle strains as resultant from the base or primary pathology.

FIGS. 20a and 20b show application of the coraco-clavicular strap 308 over the deltoid strap 306'. Clinical evidence suggests that, given a patient with separation of the acromio-clavicular joint (see, e.g., reference numeral 44 in FIG. 12c), strap 308 enhances the positioning and coming together of the coraco-clavicular as well as acromio-clavicular ligaments 44 and 46 that would ordinarily be achieved by healthy acromio-clavicular and coraco-clavicular ligaments 44 and 46 (see, e.g., FIG. 2). The patient attaches this strap 308 preferably by securing the outer attachment point first, at the lower inner border of the scapula (see FIG. 20b). From this point of origin, the opposite end of the coraco-clavicular strap 308 is pulled inclining upwardly to loop around the same-side shoulder (i.e., the right shoulder in the drawings) at about the same elevation as the acromion process, to extend from there about level with the acromion process and attach to the base 300 about in the middle of the front of the acromion process, as shown by FIG. 20a. This strap 108 is also adjustable as desired, and it most significantly gives the scapula upward and lateral support when the acromio-clavicular ligaments 44 have separated, and thus counteracts a drop in the elevation of the scapula, and subsequent medial/downward rotation, due to gravity combined with absence of support from the acromio-clavicular ligaments 44.

FIGS. 21a and 21b show application of the acromio-clavicular strap 306 over the combined coraco-clavicular and deltoid straps 308 and 306'. Clinical evidence suggests that the acromio-clavicular strap 306 enhances the positioning and coming together of the acromio-clavicular articulation that would ordinarily be achieved by healthy acromio-clavicular ligaments 44 (see, e.g., FIG. 2). The patient attaches this strap 306 preferably by securing the outer attachment point first, which is approximately behind the acromion process, or, more particularly, at the lower outer border of the rear of the acromion process. From this point of origin, the opposite end of the acromio-clavicular strap 306 is pulled in toward the patient's throat, crossing forwardly over the clavicle, to attach about in the outer portion of the front of the clavicle as shown by FIG. 21a. This strap 306 is also adjustable as desired.

FIGS. 22a and 22b show one arrangement of application of the bifurcated strap 310. In the drawings the bifurcated strap is shown applied without another strap. However, it is shown this way in the drawings merely for clarity as the bifurcated strap 310 can be used in conjunction with any other of the straps if the patient's condition so indicates.

FIGS. 22a and 22b show use of the bifurcated strap 310 to address an anteriorly (or forwardly) malpositioned (or subluxated) humeral head. The bifurcated strap has a root end 340 attached to the base 300 on the patient at a position in front of the humeral head in the shoulder socket. The branches 341 and 342 initially flare apart to cross over the top of the round of the shoulder (see FIG. 22a) but cross in the middle of the back (see FIG. 22b) and attach slightly spaced apart above the hip on the patient on the opposite side from the involved arm (i.e., the right arm and left hip as shown). Clinical evidence suggests that this arrangement of the bifurcated strap 310 enhances the positioning and coming together of an anteriorly (or forwardly) malpositioned (or subluxated) humeral head. One branch goes over the top of the shoulder while the other branch extends distal around or under the lateral acromion process, and from there crossing over the other branch at the scapula.

FIGS. 23a and 23b show an alternate arrangement of the bifurcated strap 310, which in this instance is used to address an anteriorly (or primarily forward but also somewhat cranially/upwardly and laterally/outwardly) malpositioned (or subluxated) sterno-clavicular joint. The root end 340 is attached to the base 300 on the patient at a position in front of the humeral head in the shoulder socket. The branches 341 and 342 proximately cross each other extending over the clavicle (collar bone) and sternum, and then the branches 341 and 342 diverge. One branch extends over the top of the opposite trapezius (see FIG. 23a) and then is stretched straight to attach wherever convenient on the back of the base 300 as shown in FIG. 23b. The other branch extends under the opposite arm pit (see FIG. 23a) to attach also wherever convenient on the back of the base 300, as shown by FIG. 23b. Clinical evidence suggests that this arrangement of the bifurcated strap 310 enhances the positioning and coming together of a subluxated/malpositioned sterno-clavicular joint as described above, and gives stability to that joint's motions as a patient goes through his or her day.

FIGS. 24a and 24b show application of the trapezius strap 302. Clinical evidence suggests that it enhances the positioning of and pull on the scapula ordinarily achieved by the middle and lower fibers of a healthy trapezius muscle 48 (see, e.g., FIG. 3). The trapezius strap 302 preferably is located with one end approximately on the front of the acromion process of the scapula, as shown in FIG. 24a. From this origin, the trapezius strap 302 is looped behind the back of the patient and under the uninvolved arm pit, as shown in FIG. 24b, to be secured to the base garment 300 as shown with reference back to FIG. 24a again.

FIG. 25 shows application of what is previously referred to the coraco-clavicular strap 308 over the trapezius strap 302 in the middle of the back of the patient. As used here, the coraco-clavicular strap 308 gives more adduction to the scapula, or that is, gives a pull to the scapula inwards to provide resistance against (and hence support thereof) upward rotation of the scapula.

FIGS. 26a through 26c show application of an extra strap which in this instance is the strap 304 that has been previously used to provide rhomboid support (i.e., see rhomboid strap 104 and FIGS. 9a and 9b). This and FIG. 25 demonstrates the adaptability of the inventive base garment and strap system for adding more straps and addressing multiple symptoms or indications in one patient. As shown in FIGS. 26a through 26c, the extra strap 304 is applied to loop over and compress against the trapezius on the opposite side of the involved arm (i.e., right arm, left trapezius). One end of the strap attaches directly over the involved-side scapula (i.e., right-side scapula, see FIG. 26b). From that origin, the extra strap 304 extends over the trapezius on the uninvolved side (i.e., left-side trapezium, see FIGS. 26a and 26c), and from there is pulled straight down to an attachment on the base garment 300 on the hip of the uninvolved side (i.e., left-side hip, see FIGS. 26a and 26c). The strap 304 as arranged provides additional support to the motions of the scapula.

It is an aspect of the foregoing base garment and strap system in accordance with the invention, that it is possible for a patient to dress into it and apply and adjust the straps alone, without aid from others. In order to achieve this aspect, the ends of the straps which attach on the back of the patient (or in otherwise unreachable places) ought to be pre-affixed before the patient dresses into the base garment 300. As an aid for this, the clinical or treating physical therapist might mark directly onto the base garment 300 and/or straps the locations where the various straps attach. Alternatively, the awkward ends of the straps might be sewn or otherwise semi-permanently affixed to the base garment 300 and/or each other (in instances where one strap attaches atop another). Either way, the object is to achieve consistency for where the patient starts with the first-attached ends of the straps to the base garment. If done properly, then all the tag ends (e.g., loose ends) of the straps ought to secure or fasten in front of the patient, where he or she can do this alone in order to complete application/adjustment of the straps.

FIGS. 7, 14a and 16 depict alternative arrangements of a base garment 100, 200 and/or 300 for attachment of various auxiliary straps 102 (302), 106 (306), 104 (304), 108 (308), 206, 306', and 310 for purposes described above. The FIGS. 7 and 16 base garment(s) 100 and 300 were disclosed more in connection with scapular stabilization than the FIGS. 14a base garment 200, which was more or less disclosed in connection with posture support and/or enhancement. The base garments 100, 200 and/or 300 of FIGS. 7, 14a and 16 are interchangeable substitutes for one another, and each works effectively in performing the functions that have been more particularly described in connection with one of the others.

The invention having been disclosed in connection with the foregoing variations and examples, additional variations will now be apparent to persons skilled in the art. The invention is not intended to be limited to the variations specifically mentioned, and accordingly reference should be made to the appended claims rather than the foregoing discussion of preferred examples, to assess the scope of the invention in which exclusive rights are claimed.

I claim:

1. An orthopedic method for treating given pathologies of an involved-side shoulder girdle of a patient including enhancing the positioning of and pull on the scapula ordinarily achieved by the middle and lower fibers of a healthy trapezius muscle, said method comprising the steps of:

applying to the patient an elastic base garment comprising at least one upper arm encircling portion, a torso encircling portion, and an arm-and-shoulder portion spanning between and interconnecting the upper arm encircling and torso encircling portions;

providing the base garment with diverse inner and outer surfaces wherein the inner surface is adapted for high friction contact with the patient's skin or a thin undergarment worn by the patient, the outer surface being provided with hook-fastener securing areas;

providing the torso encircling portion with one and another belt straps, one of which belt straps has hook fasteners, said belt straps allowing releasable formation of a belt around the patient's torso underneath and clear of the breasts;

providing a trapezius strap having at least one tag end carrying hook fasteners, and extending from the at least one tag end to an opposite end;

affixing said opposite end to the base garment in the front of the acromion process of the scapula of the patient on his or her involved side;

extending the trapezius strap from the affixed opposite end to loop over the trapezius and across behind the back of the patient to underneath the uninvolved arm pit; and, securing the tag end to the base garment in the front of the patient at an elevation lower than the breasts, wherein the trapezius strap is arranged to provide compression against the patient in order to position and pull on the scapula as ordinarily achieved by the middle and lower fibers of a trapezius muscle, and is elastic which allows adjusting the compression against the patient in order to sufficiently enhance the positioning of and pull on the scapula ordinarily achieved by the middle and lower fibers of a healthy trapezius muscle.

2. The orthopedic method of claim 1, wherein at least one of the tag end and the opposite end of the trapezius strap is affixed or secured relative to the base garment by means of directly affixing or securing such end of the trapezius strap to the base garment.

3. The orthopedic method of claim 1, wherein the upper arm encircling portion comprises one and another sleeve-forming straps, one of which sleeve-forming straps has hook fasteners, said sleeve-forming straps allowing releasable formation of a sleeve around the patient's upper arm between the elbow and the arm pit.

4. The orthopedic method of claim 1, further comprising:

applying an elastic tension-relieving strap to the base garment, which strap has one attachment point on the base on the outside of the upper encircling arm portion a least low on, and has a spaced attachment point on the arm-and-shoulder portion on top of the shoulder, wherein the tension-relieving strap provides relief to the tension in the muscles connected to and responsible for moving the scapula as well as obviates compensation from accessory muscles such as ones that move the upper arm.

5. The orthopedic method of claim 4, wherein the tension relieving strap substantially overlies the deltoid muscle.

6. The orthopedic method of claim 4, further comprising:

providing a rhomboid strap having a distal end carrying hook fasteners, and extending from the distal end to a base end;

affixing said base end to the base garment at a position on the patient's back and over the lower outer margin of the scapula when the scapula is in its rest position for an erect standing posture, and with arms down;

extending the rhomboid strap from the affixed opposite end to loop over and across the crotch of the neck and shoulder on the uninvolved side; and, securing the tag end to the base garment at a location in the front of the patient down from where the rhomboid strap crosses over the uninvolved-side neck and shoulder, wherein the rhomboid strap is arranged to provide compression against the patient in order to position and pull on the scapula as ordinarily achieved by rhomboid muscles, and is elastic which allows adjusting the compression against the patient in order to sufficiently enhance the positioning of and pull on the scapula ordinarily achieved by healthy rhomboid muscles.

7. An orthopedic method for treating given pathologies of an involved-side shoulder girdle of a patient including enhancing the positioning of and pull on the scapula as ordinarily achieved by healthy rhomboid muscles, said method comprising the steps of:

applying to the patient an elastic base garment comprising at least one upper arm encircling portion, a torso encircling portion, and an arm-and-shoulder portion spanning between and interconnecting the upper arm encircling and torso encircling portions;

providing the base garment with diverse inner and outer surfaces wherein the inner surface is adapted for high friction contact with the patient's skin or a thin undergarment worn by the patient, the outer surface being provided with hook-fastener securing areas;

providing the torso encircling portion with one and another belt straps, one of which belt straps has hook fasteners, said belt straps allowing releasable formation of a belt around the patient's torso underneath and clear of the breasts;

providing a rhomboid strap having at least one tag end carrying hook fasteners, and extending from the at least one tag end to an opposite end;

affixing said opposite end to the base garment at a position on the patient's back and over the lower outer margin of the scapula when the scapula is in its rest position for an erect standing posture, and with arms down;

extending the rhomboid strap from the affixed opposite end to loop over and across the crotch of the neck and shoulder on the uninvolved side; and, securing the tag end to the base garment at a location in the front of the patient down from where the rhomboid strap crosses over the uninvolved-side neck and shoulder, wherein the rhomboid strap is arranged to provide compression against the patient in order to position and pull on the scapula as ordinarily achieved by rhomboid muscles, and is elastic which allows adjusting the compression against the patient in order to sufficiently enhance the positioning of and pull on the scapula ordinarily achieved by healthy rhomboid muscles.

8. The orthopedic method of claim 4, wherein at least one of the tag end and the opposite end of the rhomboid strap is affixed or secured relative to the base garment by means of directly affixing or securing such end of the rhomboid strap to the base garment.

9. The orthopedic method of claim 4, wherein the upper arm encircling portion comprises one and another sleeve-forming straps, one of which sleeve-forming straps has hook fasteners, said sleeve-forming straps allowing releasable formation of a sleeve around the patient's upper arm between the elbow and the arm pit.

10. An orthopedic method for treating given pathologies of an involved-side shoulder girdle of a patient including—given a patient with separation of the acromio-clavicular joint—enhancing the positioning and coming together of the coraco-clavicular as well as acromio-clavicular ligaments that would ordinarily be achieved by healthy acromio-clavicular and coraco-clavicular ligaments, said method comprising the steps of:

applying to the patient an elastic base garment comprising at least one upper arm encircling portion, a torso encircling portion, and an arm-and-shoulder portion spanning between and interconnecting the upper arm encircling and torso encircling portions;

providing the base garment with diverse inner and outer surfaces wherein the inner surface is adapted for high friction contact with the patient's skin or a thin undergarment worn by the patient, the outer surface being provided with hook-fastener securing areas;

providing the torso encircling portion with one and another belt straps, one of which belt straps has hook fasteners, said belt straps allowing releasable formation of a belt around the patient's torso underneath and clear of the breasts;

providing a coraco-clavicular strap having at least one tag end carrying hook fasteners and extending from the at least one tag end to an opposite end;

affixing said opposite end to the base garment on the back of the patient at the lower inner border of the scapula on the involved side;

extending the coraco-clavicular strap from the affixed opposite end to extend inclining upwardly to loop around the same- or involved-side shoulder, at about the same elevation as the acromion process, to extend from there about level with the acromion process; and, securing the tag end to the base garment at about in the middle of the front of the acromion process on the involved side, wherein the coraco-clavicular strap is arranged to provide compression against the patient in order to position and induce the coming together of a separated acromio-clavicular joint as would ordinarily be achieved by acromio-clavicular and coraco-clavicular ligaments, and is elastic which allows adjusting the compression against the patient in order to enhance the positioning and coming together of the coraco-clavicular as well as acromio-clavicular ligaments of a separated acromio-clavicular joint that would ordinarily be achieved by healthy acromio-clavicular and coraco-clavicular ligaments.

11. The orthopedic method of claim 10, wherein at least one of the tag end and the opposite end of the coraco-clavicular strap is affixed or secured relative to the base garment by means of directly affixing or securing such end of the coraco-clavicular strap to the base garment.

12. The orthopedic method of claim 10, wherein the upper arm encircling portion comprises one and another sleeve-forming straps, one of which sleeve-forming straps has hook fasteners, said sleeve-forming straps allowing releasable formation of a sleeve around the patient's upper arm between the elbow and the arm pit.

13. The orthopedic method of claim 10, further comprising:

applying an elastic tension-relieving strap to the base garment, which strap has one attachment point on the base on the outside of the upper encircling arm portion at least low on, and has a spaced attachment point on the arm-and-shoulder portion on top of the shoulder, wherein the tension-relieving strap provides relief to the tension in the muscles connected to and responsible for moving the scapula as well as obviates compensation from accessory muscles such as ones that move the upper arm.

14. The orthopedic method of claim 13, wherein the tension relieving strap substantially overlies the deltoid muscle.

15. The orthopedic method of claim 13, further comprising:

provding an acromio-clavicular strap having opposite ends carrying hook fasteners;

securing one of said opposite ends to the base garment approximately behind the acromion process on the involved side at the lower outer border of the rear of the involved-side acromion process; and, securing the other of said opposite ends to the base garment about in the middle of the front of the clavicle on the involved side, wherein the acromio-clavicular strap is extended between said opposite ends crossing over the involved-side clavicle, is arranged to provide compression against the patient in order to position and induce the coming together of the acromio-clavicular articulation as ordinarily achieved by acromio-clavicular ligaments, and is elastic which allows adjusting the compression against the patient in order to sufficiently enhance the positioning and coming together of the acromio-clavicular articulation as ordinarily achieved by healthy acromio-clavicular ligaments.

16. An orthopedic method for treating given pathologies of an involved-side shoulder girdle of a patient including enhancing the positioning and coming together of a generally anteriorly malpositioned or subluxated sterno-clavicular joint, said method comprising the steps of:

applying to the patient an elastic base garment comprising at least one upper arm encircling portion, a torso encircling portion, and an arm-and-shoulder portion spanning between and interconnecting the upper arm encircling and torso encircling portions;

providing the base garment with diverse inner and outer surfaces wherein the inner surface is adapted for high friction contact with the patient's skin or a thin undergarment worn by the patient, the outer surface being provided with hook-fastener securing areas;

providing the torso encircling portion with one and another belt straps, one of which belt straps has hook fasteners, said belt straps allowing releasable formation of a belt around the patient's torso underneath and clear of the breasts;

providing a strap having a root end and a tag end carrying hook fasteners;

affixing said root end to the base garment at a position in front of the humeral head of the involved-side shoulder;

extending the strap from the root end over the involved-side clavicle, and at about the sternum it extends relatively down to under the opposite or uninvolved-side arm pit; and, securing the tag end to the base garment wherever convenient on the back of the patient, wherein the strap is arranged to provide compression against the patient in order to position and induce the coming together of a generally anteriorly malpositioned or subluxated sterno-clavicular joint, and is elastic which allows adjusting the compression against the patient in order to sufficiently enhance the positioning and coming together of a generally anteriorly malpositioned or subluxated sterno-clavicular joint.

17. The orthopedic method of claim 16, wherein the upper arm encircling portion comprises one and another sleeve-forming straps, one of which sleeve-forming straps has hook fasteners, said sleeve-forming straps allowing releasable formation of a sleeve around the patient's upper arm between the elbow and the arm pit.

* * * * *